(12) United States Patent
Tanaka et al.

(10) Patent No.: US 8,036,555 B2
(45) Date of Patent: Oct. 11, 2011

(54) LIQUID MEASURING DEVICE WITH FLOATING MEMBER HAVING MAGNETIC FIELD GENERATORS

(75) Inventors: Hiroshi Tanaka, Matsumoto (JP); Ken Ikuma, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 603 days.

(21) Appl. No.: 12/196,397

(22) Filed: Aug. 22, 2008

(65) Prior Publication Data

US 2009/0060546 A1  Mar. 5, 2009

(30) Foreign Application Priority Data

Aug. 30, 2007 (JP) ................................. 2007-224228
Jun. 26, 2008 (JP) ................................. 2008-167191

(51) Int. Cl.
*G03G 15/10* (2006.01)
(52) U.S. Cl. ........................................................ 399/57
(58) Field of Classification Search .................... 399/57, 399/237, 238; 73/308, 313, 314, 320
See application file for complete search history.

(56) References Cited

U.S. PATENT DOCUMENTS

| | | | | |
|---|---|---|---|---|
| 4,744,808 A | * | 5/1988 | Treu ................................ | 73/313 |
| 4,955,231 A | * | 9/1990 | Mahoney ........................ | 73/313 |
| 5,156,048 A | * | 10/1992 | DeFigueiredo et al. ........ | 73/308 |
| 5,724,629 A | | 3/1998 | Iino et al. | |
| 6,278,850 B1 | | 8/2001 | Park | |
| 6,687,477 B2 | | 2/2004 | Ichida et al. | |
| 6,876,822 B2 | | 4/2005 | Sasaki et al. | |
| 7,231,821 B2 | * | 6/2007 | Fling et al. ...................... | 73/320 |
| 7,778,576 B2 | | 8/2010 | Tanjo et al. | |
| 7,885,565 B2 | | 2/2011 | Sasaki et al. | |
| 2003/0016962 A1 | | 1/2003 | Teraoka et al. | |
| 2009/0053407 A1 | | 2/2009 | Inukai et al. | |
| 2009/0060546 A1 | | 3/2009 | Tanaka et al. | |
| 2009/0110424 A1 | | 4/2009 | Tanaka et al. | |

FOREIGN PATENT DOCUMENTS

| | | |
|---|---|---|
| JP | 09243559 A | 9/1997 |
| JP | 2000249653 A | 9/2000 |
| JP | 2002-014541 | 1/2002 |

\* cited by examiner

*Primary Examiner* — William J Royer
(74) *Attorney, Agent, or Firm* — DLA Piper LLP (US)

(57) ABSTRACT

A liquid measuring device includes a floating member that is moved in accordance with a liquid surface, a first magnetic field generator that is disposed in the floating member and positions its north (N) pole to face a first direction, a second magnetic field generator that is disposed in the floating member to be spaced apart from the first magnetic field generator and positions its south (S) pole to face the first direction, and a plurality of proportional output-type hole elements that detect magnetic fields generated by the first magnetic field generator and the second magnetic field generator in positions facing the first direction.

16 Claims, 20 Drawing Sheets

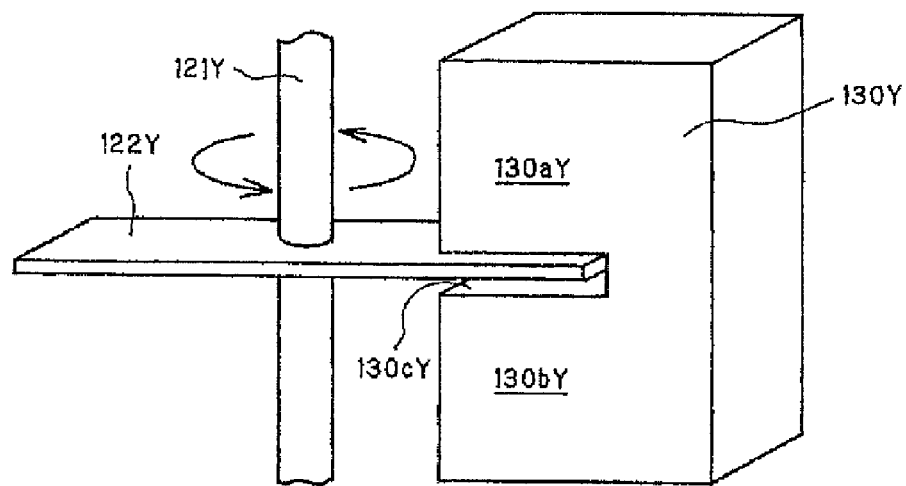
FIG.11
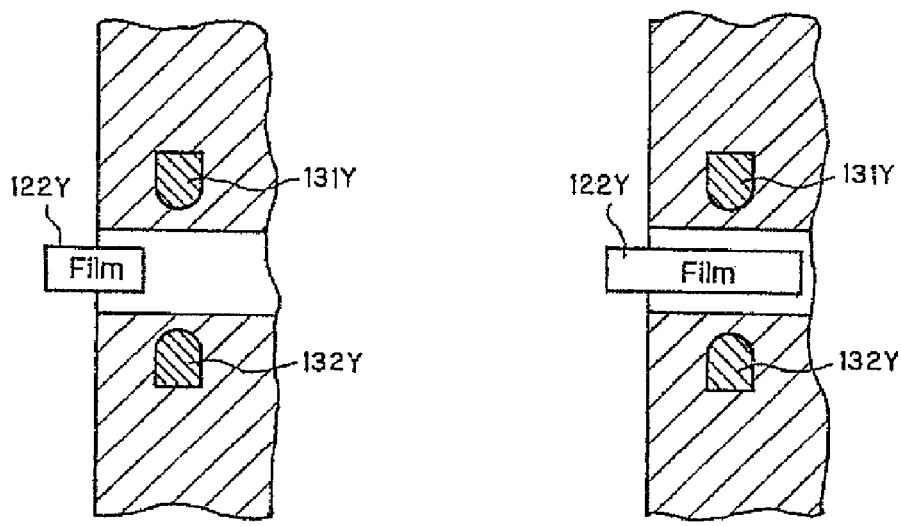
FIG.12A
FIG.12B

LIQUID MEASURING DEVICE WITH FLOATING MEMBER HAVING MAGNETIC FIELD GENERATORS

BACKGROUND

1. Technical Field

The present invention relates to a liquid measuring device, a liquid developer storing apparatus, and an image forming apparatus capable of measuring the liquid amount of liquid toner acquired from dispersing toner into a carrier liquid.

2. Related Art

Generally, a float-type liquid level sensor in which a floating member formed horizontally is moved vertically in accordance with a change of the liquid level of liquid developer while being fixed to both end parts, and a magnetic field generator is fixed in the center position of the end parts has been known (see JP-A-2002-14541). The float-type liquid level sensor includes ring pins that hold ring parts between the end parts and the center position and a plurality of guide poles that are inserted into the ring parts so as to guide the vertical movement of the floating member. In the float-type liquid level sensor, a distance between the magnetic field generator and a hole element is changed in accordance with the vertical movement of the floating member, and the liquid level is detected based on the result of detection of the hole element.

However, according to the technology disclosed in JP-A-2002-14541, the liquid level is measured in a stepped manner, and thus the amount of shortage of the liquid cannot be detected as a continuous value. Accordingly, an appropriate amount of the liquid cannot be supplied. Thus, the range of changes in the liquid level becomes wide, and overshoot increases. Accordingly, a time required for reaching a target density or target liquid level becomes long. In addition, when the liquid level is high, overflow of the liquid or the like may occur in a liquid supplying process.

SUMMARY

An advantage of some aspects of the invention is that it provides a liquid measuring device, a liquid developer storing apparatus, and an image forming apparatus capable of precisely measuring the liquid level.

According to a first aspect of the invention, there is provided a liquid measuring device including: a floating member that is moved in accordance with a liquid surface; a first magnetic field generator that is disposed in the floating member and positions its north (N) pole to face a first direction; a second magnetic field generator that is disposed in the floating member to be spaced apart from the first magnetic field generator and positions its south (S) pole to face the first direction; and a plurality of proportional output-type hole elements that detect magnetic fields generated by the first magnetic field generator and the second magnetic field generator in positions facing the first direction. Accordingly, the liquid level can be continuously measured in accordance with a proportional output, and the amount of shortage of the liquid can be detected as a continuous value. Therefore, the liquid level of the liquid can be precisely measured.

The above-described liquid measuring device may further include: a guiding unit that guides movement of the floating member; and a regulating member that regulates the movement of the floating member. In such a case, limit points can be detected, and thus overflow and the like can be prevented.

According to a second aspect of the invention, there is provided a liquid developer storing apparatus including: a storage unit that stores liquid developer containing toner particles in a carrier liquid; and a liquid measuring device including: a floating member that is moved in accordance with a liquid surface of the liquid developer inside the storage unit; a first magnetic field generator that is disposed in the floating member and positions its north (N) pole to face a first direction; a second magnetic field generator that is disposed in the floating member to be spaced apart from the first magnetic field generator and positions its south (S) pole to face the first direction; and a plurality of proportional output-type hole elements that detect magnetic fields generated by the first magnetic field generator and the second magnetic field generator in positions facing the first direction. Accordingly, the liquid level of the liquid developer can be continuously measured in accordance with the proportional output, and the amount of shortage of the liquid developer can be detected as a continuous value. Therefore, the liquid level of the liquid developer can be measured precisely.

The above-described liquid developer storing apparatus may further have a density measuring device including: a moving member that can be moved within the storage unit; a light emitting member; a light receiving member that receives light emitted by the light emitting member; a gap part in which the moving member can be moved between the light emitting member and the light receiving member; and a density measuring unit that measures the density of the liquid developer based on the output of the light receiving member for a case where the moving member is located in the gap part and a case where the moving member is not located in the gap part. In such a case, the liquid developer can be precisely adjusted to have the liquid amount and density that are needed.

The above-described liquid developer storing apparatus may further include: a guiding unit that guides the movement of the floating member; and a regulating member that is disposed in the density measuring unit and regulates the movement of the floating member. In such a case, limit points can be detected, and thus overflow and the like can be prevented.

According to a third aspect of the invention, there is provided an image forming apparatus including: a developer container; a developer carrier that carries liquid developer; a developer supplying member that supplies the liquid developer stored in the developer container to the developer carrier; an image carrier on which a latent image is developed by the developer carrier; a transfer body on which the image on the image carrier is transferred; a storage unit in which the liquid developer is stored; and a liquid measuring device. The liquid measuring device includes: a floating member that is moved in accordance with a liquid surface of the liquid developer inside the storage unit; a first magnetic field generator that is disposed in the floating member and positions its north (N) pole to face a first direction; a second magnetic field generator that is disposed in the floating member to be spaced apart from the first magnetic field generator and positions its south (S) pole to face the first direction; and a plurality of proportional output-type hole elements that detect magnetic fields generated by the first magnetic field generator and the second magnetic field generator in positions facing the first direction. In such a case, the amount of shortage of the liquid developer can be detected as a continuous value by continuously measuring the liquid level of the liquid developer in accordance with a proportional output. In addition, the liquid level of the liquid developer can be precisely detected. Therefore, an image having an excellent image quality can be formed.

The above-described image forming apparatus may further include a position adjusting mechanism that adjusts a position of the liquid measuring device in the vertical direction. In such a case, the degree of freedom for design can be increased.

The above-described image forming apparatus may further include a supply path through which the liquid developer is supplied from the storage unit of the liquid developer to the developer container, and the plurality of proportional output-type hole elements of the liquid measuring device may be disposed in the supply path. In such a case, the precision of detection can be improved.

The above-described image forming apparatus may further have a density measuring device including: a moving member that can be moved within the storage unit; a light emitting member; a light receiving member that receives light emitted by the light emitting member; a gap part in which the moving member can be moved between the light emitting member and the light receiving member; and a density measuring unit that measures the density of the liquid developer based on an output of the light receiving member for a case where the moving member is located in the gap part and a case where the moving part is not located in the gap part; and a wiring of the density measuring device which is disposed along the supply path. In such a case, the number of components can be decreased and the wiring can be maintained in a stable manner.

The above-described image forming apparatus may further include: a collection path through which the liquid developer is collected into the storage unit; an agitating propeller that agitates the liquid developer inside the storage unit; and an agitating propeller shaft that supports the agitating propeller to be rotatable. The agitating propeller may be disposed to be overlapped with the collection path, viewed from the direction of the agitating propeller shaft. In such a case, the liquid developer that is newly collected or supplied can be agitated in a speedy manner.

In the above-described image forming apparatus, the floating member may have an opposing face that faces the plurality of proportional output-type hole elements. In such a case, the precision of the hole elements can be improved by decreasing the flow of the liquid developer.

In the above-described image forming apparatus, the floating member may have an end part having a rounded acute-angled shape on the opposite side of the opposing face. In such a case, the liquid developer can be easily flown.

The above-described image forming apparatus may further include: a liquid-level determining unit that determines the liquid amount measured by the liquid measuring device; a liquid-level control unit that controls the liquid amount based on the result of determination of the liquid-level determining unit; a density determining unit that determines the density measured by the density measuring device; a density control unit that controls the density of the liquid developer of the storage unit in accordance with the result of determination of the density determining unit; and a selection unit that selects one between the liquid-level control unit and the density control unit. In such a case, the image forming apparatus can be controlled in accordance with the liquid amount and density of the liquid developer, and thereby an image having excellent image quality can be formed in accordance with the state of the liquid developer.

The above-described image forming apparatus may further include a sending amount calculating unit that prohibits input of the liquid by using the liquid-level control unit in a case where the liquid amount measured by the liquid measuring device is larger than a predetermined amount. In such a case, overflow and the like can be prevented.

The above-described image forming apparatus may further include a sending amount calculation unit that stops printing by using the density determining unit in a case where the density measured by the density measuring device is higher than a first predetermined density or lower than a second predetermined density that is set lower than the first predetermined density. In such a case, an image having deteriorated image quality is not formed.

BRIEF DESCRIPTION OF THE DRAWINGS

The invention will be described with reference to the accompanying drawings, wherein like numbers reference like elements.

FIG. 11 is an enlarged diagram showing a part in the vicinity of a transparent propeller shown in FIG. 10.

FIGS. 12A and 12B are enlarged views of a gap part according to an embodiment of the invention.

DESCRIPTION OF EXEMPLARY EMBODIMENTS

Figure 1:
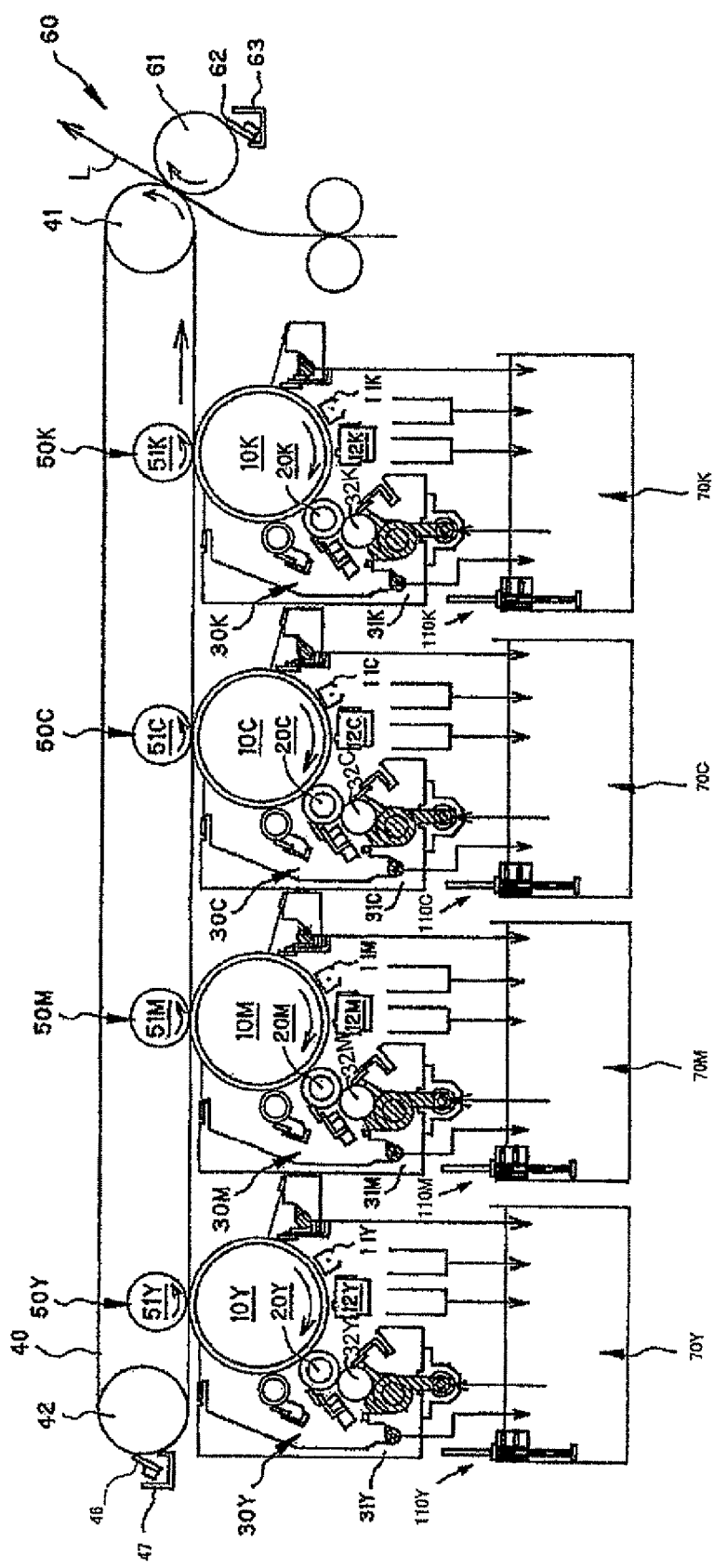
FIG. 1 is a diagram showing an image forming apparatus according to an embodiment of the invention.

Hereinafter, an embodiment of the present invention will be described with reference to the accompanying drawings. FIG. 1 is a diagram showing major elements constituting an image forming apparatus according to an embodiment of the invention. In a center part of the image forming apparatus, image forming units for each color are disposed. In addition, developing units 30Y, 30M, 30C, and 30K and developer collecting and supplying devices 70Y, 70M, 70C, and 70K are disposed in a lower part of the image forming apparatus. In addition, an intermediate transfer body 40 and a secondary transfer unit 60 are disposed in an upper part of the image forming apparatus.

The image forming units include image carriers 10Y, 10M, 10O, and 10K, corona charging units 11Y, 11M, 11C, and 11K, exposure units 12Y, 12M, 12O, and 12K, and the like. The exposure units 12Y, 12M, 12C, and 12K are constituted by line heads, in which LEDs or the like are aligned, and the like. The corona charging units 11Y, 11M, 11C, and 11K electrically charge the image carriers 10Y, 10M, 10C, and 10K in a same manner, the exposure units 12Y, 12M, 12C, and 12K emit laser beams that have been modulated based on an input image signal, and electrostatic latent images are formed on the charged image carriers 10Y, 10M, 10C, and 10K.

The developing units 30Y, 30M, 30C, and 30K include developing rollers 20Y, 20M, 20C, and 20K, developer containers 31Y, 31M, 31C, and 31K that store each one of liquid developers of colors including yellow Y, magenta M, cyan C, and black K, and developer supplying rollers 32Y, 32M, 32C, and 32K that supply each one of the liquid developers of the colors from the developer containers 31Y, 31M, 31C, and 31K to the developing rollers 20Y, 20M, 20C, and 20K. The developing units 30Y, 30M, 30C, and 30K develop the electrostatic latent images formed on the image carriers 10Y, 10M, 10C, and 10K by using the liquid developers of the colors.

The intermediate transfer body 40 is an endless belt member, The intermediate transfer body 40 is tightly wound to extend between a driving roller 41 and a tension roller 42. While being brought into contact with the image carriers 10Y, 10M, 10C, and 10K by primary transfer units 50Y, 50M, 50C, and 50K, the intermediate transfer body 40 is driven to rotate by the driving roller 41. Primary transfer rollers 51Y, 51M, 51C, and 51K of the primary transfer units 50Y, 50M, 50C, and 50K are disposed to face the image carriers 10Y, 10M, 10C, and 10K with the intermediate transfer body 40 interposed therebetween. The primary transfer units 50Y, 50M, 50C, and 50K sequentially transfer developed toner images of each color formed on the image carriers 10Y, 10M, 10C, and 10K on the intermediate transfer body 40 in a superposing manner by using contact positions between the image carriers 10Y, 10M, 10C, and 10K and the primary transfer units 50Y, 50M, 50C, and 50K as transfer positions, and thereby forming a full-color toner image.

A secondary transfer roller 61 of the secondary transfer unit 60 is disposed to face the driving roller 41 with the intermediate transfer body 40 interposed therebetween. In addition, in the secondary transfer unit 60, a cleaning device including a secondary transfer roller cleaning blade 62 and a developer collecting unit 63 is disposed. The secondary transfer unit 60 transports and supplies a sheet member such as a paper sheet, a film, or a cloth to a sheet member transporting path L in accordance with a timing at which a full-color toner image formed by superposing colors on the intermediate transfer body 40 or a monochrome toner image arrives at the transfer position of the secondary transfer unit 60 and performs a secondary transfer process for the monochrome toner image or the full-color toner image on the sheet member. On the rear side of the sheet member transporting path L, a fixing unit that is not shown in the figure is disposed. By fusing and fixing the monochrome toner image or the full-color toner image transferred on the sheet member on a recording medium (sheet member) such as a paper sheet, an operation for forming a final image on the sheet member is completed.

On the side of the tension roller 42 that tightly supports the intermediate transfer body 40 together with the driving roller 41, a cleaning device including an intermediate transfer body cleaning blade 46 and a developer collecting unit 47 which are disposed along the outer periphery of the tension roller 42 is disposed. After passing through the secondary transfer unit 60, the intermediate transfer body 40 advances to a winding part of the tension roller 42. Then, a cleaning operation for the intermediate transfer body 40 is performed by the intermediate transfer body cleaning blade 46, and the intermediate transfer body 40 advances toward the primary transfer units 50Y, 50M, 50C and 50K again.

The developer collecting and supplying devices 70Y, 70M, 70C, and 70K adjust the density of the liquid developer that has been collected from the image carriers 10Y, 10M, 10C, and 10K and the developing units 30Y, 30M, 30C, and 30K and supply the liquid developer to the developer containers 31Y, 31M, 31C, and 31K.

Figure 2:
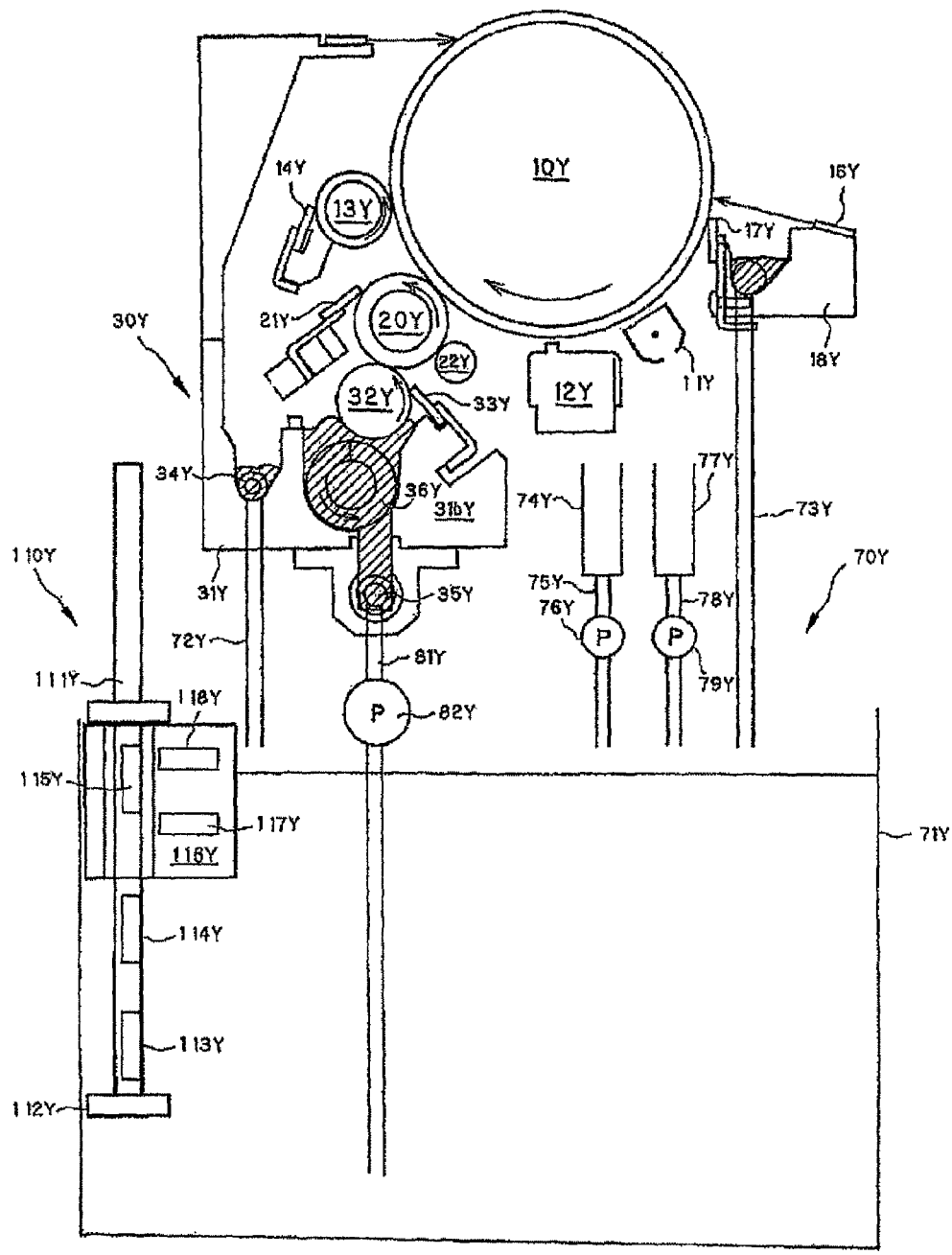
FIG. 2 is a cross-section view showing major constituent elements of an image forming unit and a developing unit according to an embodiment of the invention.
Figure 3:
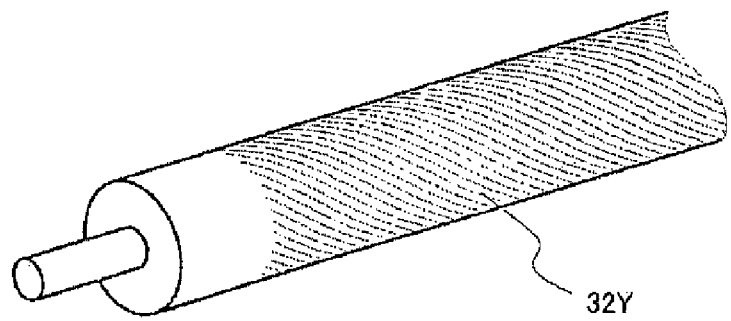
FIG. 3 is a perspective view of a developer supplying member according to an embodiment of the invention.
Figure 4:
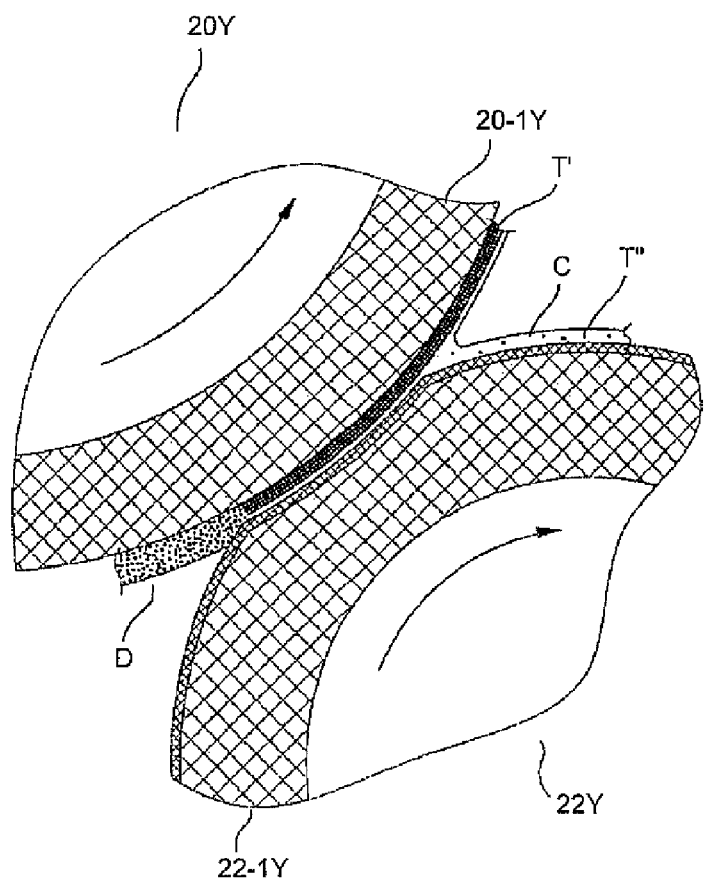
FIG. 4 is a diagram showing compression of developer performed by a developer compressing roller according to an embodiment of the invention.
Figure 5:
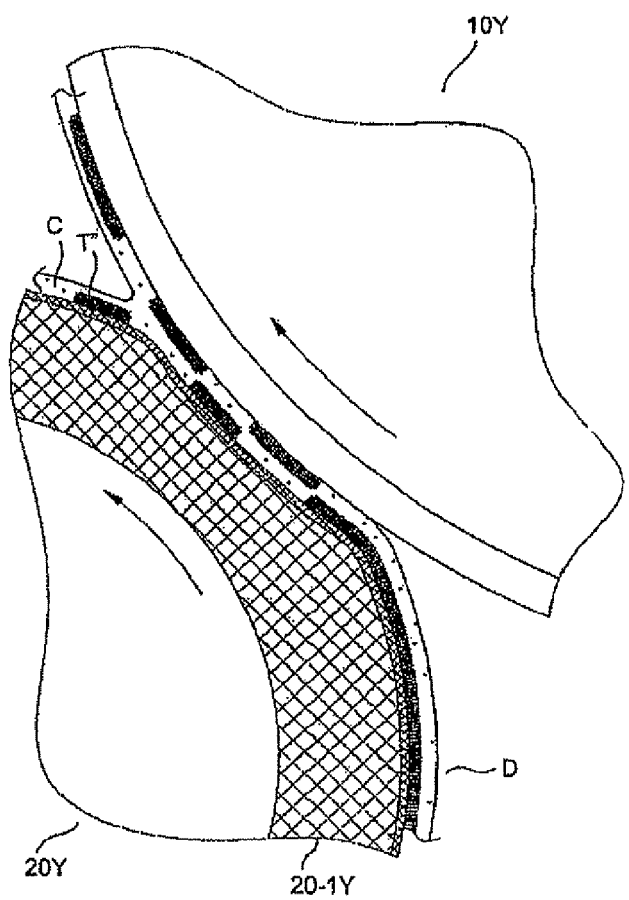
FIG. 5 is a diagram showing a developing process performed by a developing roller according to an embodiment of the invention.
Figure 6:
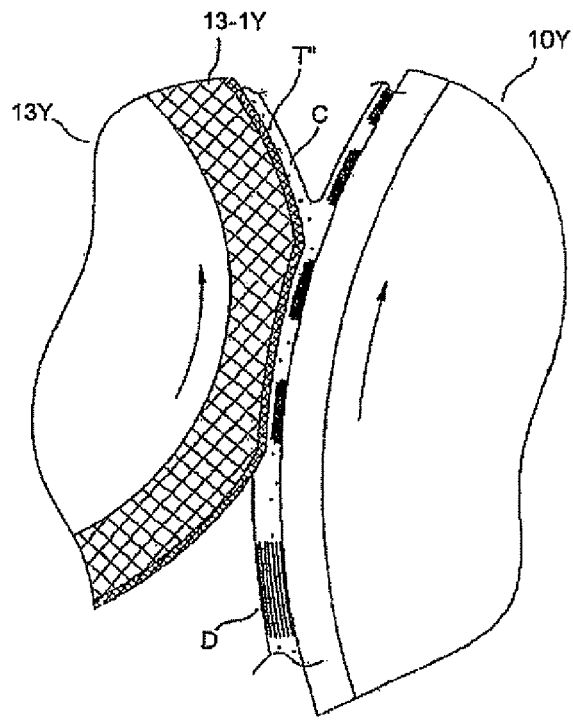
FIG. 6 is a diagram showing a squeezing operation performed by an image carrier squeezing roller according to an embodiment of the invention.

Next, the image forming units and the developing units 30Y, 30M, 30C and 30K will be described. FIG. 2 is a cross-section view showing major constituent elements of an image forming unit and a developing unit 30Y. FIG. 3 is a diagram showing a developer supplying roller or member 32Y. FIG. 4 is a diagram showing compression of the developer performed by a developer compressing roller 22Y. FIG. 5 is a diagram showing a developing process performed by the developing roller 20Y. FIG. 6 is a diagram showing a squeezing operation performed by an image carrier squeezing roller 13Y. Since the configurations of the image forming units and the developing units 30Y, 30M, 30C and 30K for each color are the same, hereinafter, an image forming unit of yellow color Y and a developing unit 30Y of yellow color Y will be described.

In the image forming unit, a neutralization device 16Y, a cleaning device including an image carrier cleaning blade 17Y and a developer collecting unit 18Y, a corona charging unit 11Y, an exposure unit 12Y, a developing roller 20Y of the developing unit 30Y, and a squeeze device including an image carrier squeezing roller 13Y and an image carrier squeezing roller cleaning blade 14Y are disposed along the rotation direction of the outer periphery of the image carrier 10Y. In addition, on the outer periphery of the developing roller 20Y of the developing unit 30Y, a developer roller cleaning blade 21Y and the developer supplying roller 32Y using an anilox roller are disposed. Inside the liquid developer container 31Y, an agitating paddle 36Y and the developer supplying roller 32Y are housed. In addition, along the intermediate transfer body 40, the primary transfer roller 51Y of the primary transfer unit 50Y is disposed in a position facing the image carrier 10Y.

The image carrier 10Y is a photosensitive drum that has a width larger than that of the developing roller 20Y by about 320 mm and is formed of a cylindrical member having a photosensitive layer formed on its outer peripheral surface. For example, the image carrier 10Y, as shown in FIG. 2, is rotated in the clockwise direction. The photosensitive layer of the image carrier 10Y is formed of an organic image carrier, an amorphous silicon image carrier, or the like. The corona charging unit 11Y is disposed on the upstream side of a nip part of the image carrier 10Y and the developing roller 20Y in the rotation direction of the image carrier 10Y. To the corona charging unit 11Y, a bias having a same polarity as the charging polarity of developing toner particles is applied by a power supply device not shown in the figure so as to charge the image carrier 10Y. The exposure unit 12Y, on the downstream side of the corona charging unit 11Y in the rotation direction of the image carrier 10Y, forms an electrostatic latent image on the image carrier 10Y by exposing the upper surface of the image carrier 10Y that is charged by the corona charging unit 11Y.

The developing unit 30Y has the developer container 31Y that stores liquid developer in a state that toner having a weight ratios of about 25% is dispersed into carrier liquid, the developing roller 20Y that carries the liquid developer, the developer supplying roller 32Y, a regulating blade 33Y, and the agitating paddle 36Y that are used for agitating the liquid developer to be maintained in a same dispersion state and supplying the liquid developer to the developing roller 20Y, a supply unit 35Y that supplies the liquid developer to the agitating paddle 36Y from a liquid developer storing unit 71Y to be described later, the developing roller cleaning blade 21Y that performs a cleaning operation for the developing roller 20Y, and a collecting screw 34Y that collects the liquid developer scraped by the developing roller cleaning blade 21Y and the image carrier squeezing roller cleaning blade 14Y and sends the collected liquid developer to the liquid developer storing unit 71Y, to be described later.

The liquid developer housed in the developer container 31Y is not generally-used volatile liquid developer having low density (about 1 to 2 wt %), low viscosity, and volatile at room temperature and using Isopar (trademark of Exxon) as a carrier liquid, but non-volatile liquid developer having high density, high viscosity, and non-volatile at room temperature. In other words, the liquid developer according to an embodiment of the invention is high-viscosity (about 30 to 10000 mPa·s) liquid developer that is prepared by adding solids having average diameter of 1 μm, in which colorants such as pigments are dispersed in a thermoplastic resin, into a liquid solvent such as an organic solvent, silicon oil, mineral oil, or cooking oil with a dispersant to have a toner solid content of about 25%.

The developer supplying roller 32Y, as shown in FIG. 3, is a cylindrical member and is an anilox roller having a corrugated surface in which delicate spiral grooves are formed so as to easily carry the developer on the surface. For example, the developer supplying roller 32Y is rotated in the clockwise direction as shown in FIG. 2. In regard to the size of the grooves, the pitch of the grooves is about 130 μm, and the depth of the grooves is about 30 μm. The liquid developer is supplied from the developer container 31Y to the developing roller 20Y by the developer supplying roller 32Y. The agitating paddle 36Y and the developer supplying roller 32Y may be brought into contact with each other in a slidable manner or may be disposed to be separated from each other.

The regulating blade 33Y is configured by an elastic blade formed by coating the surface with an elastic body, a rubber part formed of urethane rubber or the like that is brought into contact with the surface of the developer supplying roller 32Y, and a plate formed of metal or the like that supports the rubber part. The regulating blade 33Y controls the amount of the liquid developer supplied to the developing roller 20Y by regulating and controlling the film thickness and amount of the liquid developer that is carried and transported on the developer supplying roller 32Y configured by an anilox roller. The rotation direction of the developer supplying roller 32Y may not be a direction denoted by an arrow shown in FIG. 2 and may be a direction opposite thereto. In such a case, the regulating blade 33Y is needed to be disposed in correspondence with the rotation direction.

The developing roller 20Y is a cylindrical member having a width of about 320 mm and rotates about its rotation axis in the counterclockwise direction as shown in FIG. 2. The developing roller 20Y is configured by forming an elastic layer 20-1Y formed of polyurethane rubber, silicon rubber, NBR, or the like on the outer periphery of an inner core formed of metal such as iron. The developing roller cleaning blade 21Y is formed of rubber that is brought into contact with the surface of the developing roller 20Y. The developing roller 20Y is disposed on the downstream side of a developing nip part that is brought into contact with the image carrier 10Y in the rotation direction of the developing roller 20Y, and the developing roller cleaning blade 21Y scrapes and removes liquid developer remaining on the developing roller 20Y.

The developer compressing roller 22Y is a cylindrical member and, as shown in FIG. 4, similar to the developing roller 20Y, is in the form of an elastic roller configured by coating an elastic body 22-1Y. The developer compressing roller 22Y has a structure in which a conductive resin layer or a rubber layer is formed on a surface layer of a metal roller base material. For example, the developer compressing roller 22Y is, as shown in FIG. 2, rotated in the clockwise direction that is opposite to the direction of the developing roller 20Y. The developer compressing roller 22Y has a unit for increasing the charging bias of the surface of the developing roller 20Y. The developer that has been transported by the developing roller 20Y, as shown in FIGS. 2 and 4, is applied with an electric field from the developer compressing roller 22Y side to the developing roller 20Y in a developer compressing part in which the developer compressing roller 22Y is sled to be brought into contact with the developing roller 20Y to form the nip part. The unit for applying the electric field for compressing the developer may be a corona discharger that generates corona discharge instead of the roller shown in FIG. 2.

By the developer compressing roller 22Y, as shown in FIG. 4, toner T' uniformly dispersed into the carrier liquid C. is moved to be aggregated to the developing roller 20Y side, and then so-called a developer compressing state T' is formed. In addition, a part of the carrier liquid C and a small amount of toner T" that is not in the developer compressing state T' are carried and rotated in a direction denoted by an arrow shown in the figure by the developer compressing roller 22Y, are scraped to be removed by a developer compressing roller cleaning blade, and are merged with the developer inside the developer container 31Y to be reused. On the other hand, the developer D that is carried on the developing roller 20Y to be developer-compressed is, as shown in FIG. 5, in a developing nip part in which the developing roller 20Y is brought into contact with the image carrier 10Y, developed in correspondence with the latent image of the image carrier 10Y by application of a required electric field. Then, the remaining developer D after development is scraped to be removed by the developing roller cleaning blade 21Y and is merged with the developer inside the developer container 31Y to be reused. The merged carrier liquid and toner are not in a state of a mixed color.

The image carrier squeezing device is disposed on the downstream side of the developing roller 20Y to face the image carrier 10Y and collects remaining developer on the image carrier 10Y after development of a toner image. As shown in FIG. 2, the image carrier squeezing device includes the image carrier squeezing roller 13Y formed of an elastic roller member that has the surface coated with an elastic body 13-1Y (FIG. 6) and is sled to be brought into contact with the image carrier 10Y for being rotated and the image carrier squeezing roller cleaning blade 14Y that is sled to be brought into contact with the image carrier squeezing roller 13Y in a pressing manner so as to clean the surface.

The primary transfer unit 50Y transfers a developer image developed on the image carrier 10Y on the intermediate transfer body 40 by using the primary transfer roller 51Y. Here, a configuration in which the image carrier 10Y and the intermediate transfer body 40 are moved at a constant speed is used. Accordingly, driving load for rotation and movement is reduced, and disturbance of the developed toner image due to the image carrier 10Y is suppressed.

The developer collecting and supplying device 70Y has the liquid developer storing unit 71Y that stores the collected liquid developer and controls density of the liquid developer by supplying high-density developer from a developer tank 74Y and a carrier liquid from a carrier liquid tank 77Y, as an example of a container unit.

In this embodiment, the liquid developer is collected from the developing unit 30Y and the image carrier 10Y. The liquid developer collected by the developer collecting screw 34Y of the developing unit 30Y is collected into the liquid developer storing unit 71Y through a developing unit collecting path 72Y. In addition, the liquid developer collected by the cleaning device that is configured by the image carrier cleaning blade 17Y and the developer collecting unit 18Y from the image carrier 10Y is collected into the liquid developer storing unit 71Y through an image carrier collecting path 73Y.

In addition, the high-density developer is supplied from the developer tank 74Y to the liquid developer storing unit 71Y through a developer supplying path 75Y and a developer pump 76Y. The carrier liquid is supplied from the carrier liquid tank 77Y to the liquid developer storing unit 71Y through a carrier liquid supplying path 78Y and a carrier liquid pump 79Y. A structure in which the developer or the carrier liquid is supplied by opening or closing a valve or the like using gravity instead of the pump and the like may be used.

The liquid developer stored in the liquid developer storing unit 71Y is supplied to the developer container 31Y through a developer supplying path 81Y and a developer supplying pump 82Y.

Next, the operation of the image forming apparatus according to an embodiment of the invention will be described. Subsequently, in regard to the image forming units and the developing units 30Y, 30M, 30C and 30K, the image forming unit of yellow color and the developing unit 30Y from among the four image forming units and the developing units 30Y, 30M, 30C and 30K will be described as examples.

In the developer container 31Y, toner particles inside the liquid developer have positive charges. The liquid developer is pumped from the developer container 31Y by agitating the liquid developer by using the agitating paddle 36Y to rotate the developer supplying roller 32Y.

The regulating blade 33Y is brought into contact with the surface of the developer supplying roller 32Y, leaves liquid developer inside the anilox-patterned grooves that are formed on the corrugated surface of the developer supplying roller 32Y, and scrapes other remaining liquid developer. Accordingly, the regulating blade 33Y regulates the amount of liquid developer to be supplied to the developing roller 20Y. By the above-described regulating operation, the film thickness of liquid developer coated on the developing roller 20Y is quantified to be about 6 μm. Then, the liquid developer scraped by the regulating blade 33Y is fallen to be returned to the developer container 31Y by gravity. On the other hand, liquid developer that has not been scraped by the regulating blade 33Y is stored in the grooves of corrugated surface of the developer supplying roller 32Y and is pressed by the developing roller 20Y, and accordingly, the liquid developer is coated on the surface of the developing roller 20Y.

The developing roller 20Y on which the liquid developer is coated by the developer supplying roller 32Y is brought into contact with the developer compressing roller 22Y on the downstream of a nip part between the developer supplying roller 32Y and the developing roller 20Y. To the developing roller 20Y, a bias of about +400 V is applied. In addition, to the developer compressing roller 22Y, a bias that is higher than that of the developing roller 20Y and has a same polarity as the charging polarity of the toner is applied. For example, to the developer compressing roller 22Y, a bias of about +600 V is applied. Accordingly, toner particles inside the liquid developer on the developing roller 20Y, as shown in FIG. 4, are moved to the developing roller 20Y side at the moment when the toner particles pass the nip between the developer compressing roller 22Y and the developing roller 20Y. Accordingly, a state that the toner particles are gently combined together and formed as a film is formed. Thus, in a developing process at the image carrier 10Y, the toner particles are moved from the developing roller 20Y to the image carrier 10Y in a prompt manner, and thereby the image density is improved.

The image carrier 10Y is formed of amorphous silicon. After the surface of the image carrier 10Y is charged at about +600 V by the corona charging unit 11Y on the upstream of a nip part between the developing roller 20Y and the image carrier 10Y, a latent image is formed on the image carrier 10Y, so that the electric potential of the image part is set to +25 V by the exposure unit 12Y. In the developing nip part formed between the developing roller 20Y and the image carrier 10Y, as shown in FIG. 5, the toner T is selectively moved to the image part on the image carrier 10Y in accordance with an electric field formed by the bias of +400 V applied to the developing roller 20Y and the latent image (image part +25 V, non-image part +600 V) on the image carrier 10Y, and thereby a toner image is formed on the image carrier 10Y. In addition, since the carrier liquid C is not influenced by the electric field, as shown in FIG. 5, the carrier liquid is divided at the outlet of the developing nip part of the developing roller 20Y and the image carrier 10Y, and thus, the carrier liquid is adhered to both the developing roller 20Y and the image carrier 10Y.

The image carrier 10Y passing through the developing nip part passes though the image carrier squeezing roller 13Y part. The image carrier squeezing roller 13Y, as shown in FIG. 6, has a function for increasing the toner particle ratio of a developed image by collecting the remaining carrier liquid C from the developer D developed on the image carrier 10Y and originally unnecessary redundant toner T". The capability of collecting the remaining carrier liquid C can be set to a required level by using the rotation direction of the image carrier squeezing roller 13Y and a relative difference of the circumferential velocity of the surface of the image carrier squeezing roller 13Y with respect to the circumferential velocity of the surface of the image carrier 10Y. When the image carrier squeezing roller 13Y is rotated in a counter direction with respect to the image carrier 10Y, the collection capability increases. In addition, as the above-described difference between the circumferential velocities is set to be large, the collection capability increases, and thus, an additional synergetic effect can be acquired.

In this embodiment, as an example, the image carrier squeezing roller 13Y is rotated at an approximately same circumferential velocity as that of the image carrier 10Y as shown in FIG. 6 and a redundant carrier liquid C having a weight ratio of about 5 to 10% is collected from the developer D developed on the image carrier 10Y. Accordingly, both loads for driving rotation are reduced, and disturbance of the developed toner image due to the image carrier 10Y is suppressed. The redundant carrier liquid C and the unnecessary redundant toner T" that have been collected by the image carrier squeezing roller 13Y are collected from the image carrier squeezing roller 13Y into the developer container 31Y by the operation of the image carrier squeezing roller cleaning blade 14Y. In addition, since the redundant carrier liquid C and the redundant toner T" collected as described above are collected from an isolated dedicated image carrier 10Y, a phenomenon of color mixture does not occur in all the spots.

Next, the image carrier 10Y passes the nip part between the intermediate transfer body 40 and the image carrier 10Y, so that the primary transfer of the developed toner image onto the intermediate transfer body 40 is performed by the primary transfer unit 50Y. To the primary transfer roller 51Y, about −200 V having a polarity opposite to that of the charged polarity of the toner particles is applied, and accordingly the toner is primary transferred onto the intermediate transfer body 40 from the image carrier 10Y, and only the carrier liquid remains on the image carrier 10Y. On the downstream side of the primary transfer unit 50Y in the rotation direction of the image carrier 10Y, the electrostatic latent image is eliminated from the image carrier 10Y after the primary transfer by the neutralization device 16Y formed of LEDs or the like. Then, the remaining carrier liquid on the image carrier 10Y is scraped off by the image carrier cleaning blade 17Y and is collected to the developer collecting unit 18Y.

The toner image formed on the intermediate transfer body 40 which is carried in a superposing manner by primary transferring toner images formed on a plurality of image carriers 10Y, 10M, 10C and 10K one after another advances to the secondary transfer unit 60 and enters into the nip part between the intermediate transfer body 40 and the secondary transfer roller 61. The width of the nip part is set to 3 mm. In the secondary transfer unit 60, −1200 V is applied to the secondary transfer roller 61, and +200 V is applied to the driving roller 41. Accordingly, the toner image on the intermediate transfer body 40 is transferred onto a recording medium (sheet member) such as a paper sheet.

However, when a trouble in supplying the sheet member such as a jam occurs, not all the toner images are transferred onto the secondary transfer roller 61 to be collected, and a part of the toner images remains on the intermediate transfer body 40. In addition, in an ordinary secondary transfer process, not 100% of the toner image formed on the intermediate transfer body 40 is secondary transferred to be transited onto the sheet member, and several percentages of secondary transfer remaining occurs. In particular, when a trouble in supplying the sheet member such as a jam occurs, the toner image is brought into contact with the secondary transfer roller 61 to be transferred in a state that the sheet member is not interposed therebetween, and thus the rear surface of the sheet member gets dirty. In a process not for transferring the unnecessary toner images, in this embodiment, a bias that is in the direction for pressing the toner particles of the liquid developer to the intermediate transfer body 40 and has a same polarity as the charged polarity of the toner particles is applied to the secondary transfer roller 61. Accordingly, the toner particles of the liquid developer remaining on the intermediate transfer body 40 is pressed to the intermediate transfer body 40 side to be in a compaction state, and the carrier liquid is collected (squeezed) at the secondary transfer roller 61 side, Then a cleaning operation for the surface of the intermediate transfer body 40 is performed by using the intermediate transfer body cleaning blade 46, and a cleaning operation for the surface of the secondary transfer roller 61 is performed by using the secondary transfer roller cleaning blade 62 is performed.

Next, the cleaning device of the intermediate transfer body 40 will be described. When a trouble in supplying the sheet member such as a jam occurs, not all the toner images are transferred onto the secondary transfer roller 61 to be collected, and thus, a part of the toner images remains on the intermediate transfer body 40. In addition, in an ordinary secondary transfer process, not 100% of the toner image formed on the intermediate transfer body 40 is secondary transferred to be transited onto the sheet member, and several percentages of secondary transfer remaining occurs. These two types of the unnecessary toner images are collected by the intermediate transfer body cleaning blade 46 and the developer collecting unit 47 that are disposed to be brought into contact with the intermediate transfer body 40 for forming the next image. In such a non-transfer process, a bias for pressing the remaining toner on the intermediate transfer body 40 to the intermediate transfer body 40 is applied to the secondary transfer roller 61.

Next, a liquid measuring device 110Y will be described. As shown in FIG. 1, the image forming apparatus also includes similar liquid measuring devices 110M, 110C and 110K, As shown in FIG. 2, the liquid measuring device 110Y has a float supporting member 111Y, a regulating member 112Y, a first hole element 113Y as an example of a proportional output-type hole element, a second hole element 114Y, a third hole element 115Y, a float 116Y as an example of a floating member, and first and second magnetic field generators 117Y and 118Y.

The float supporting member 111Y is formed of a member that supports the float 116Y to be movable from a position on the liquid surface inside the liquid developer storing unit 71Y to an approximate bottom part below the liquid surface. On the upper side of the float supporting member 111Y, an upper regulating member is disposed, and a lower regulating member is disposed on the lower side of the float supporting member 111Y. In addition, between the lower regulating member and the upper regulating member, the first hole element 113Y, the second hole element 114Y, and the third hole element 115Y are sequentially disposed from the bottom with a predetermined distance apart therebetween.

The first hole element 113Y, the second hole element 114Y, and the third hole element 115Y are formed of proportional output-type hole elements of which output voltage changes in accordance with magnetic flux density. In this embodiment, the distance between the hole elements is set to 30 mm.

The float 116Y is a member that is movable relative to the float supporting member 111Y by floating on the liquid surface in accordance with the position of the liquid surface. On the lower side of the float 116Y, the first magnetic field generator 117Y is disposed, and the second magnetic field generator 118Y is disposed on the upper side thereof to be a predetermined distance apart from the first magnetic field generator 117Y.

The first magnetic field generator 117Y and the second magnetic field generator 118Y are disposed to be moved in accordance with movement of the float 116Y while facing the hole elements 113Y, 114Y, and 115Y. The first magnetic field generator 117Y and the second magnetic field generator 118Y are disposed to have the north (N) pole and the south (S) pole disposed on opposite sides. in this embodiment, the magnetic field generators 117Y and 118Y having a diameter of 5 mm, a length of 6 mm, and 4000 Gauss are disposed to be spaced apart by 20 mm.

Hereinafter, a method of converting outputs of the hole elements 113Y, 114Y, and 115Y into distances in a case where the above-described liquid measuring device 110Y is actually operated will be described.

Figure 7:
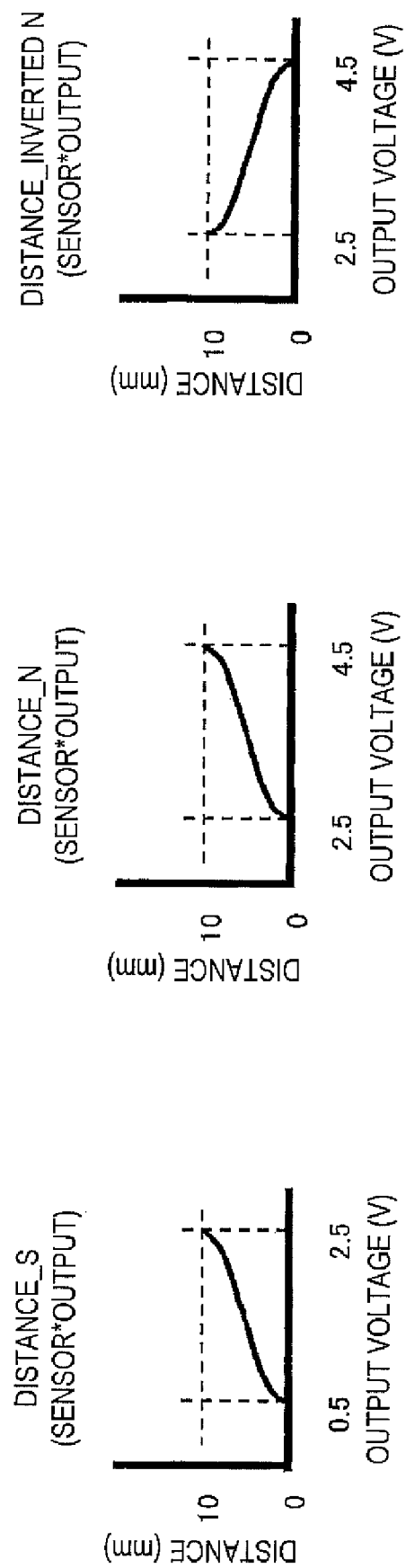
FIGS. 7A, 7B, and 7C are diagrams showing tables used for converting outputs of hole elements into a distance according to an embodiment of the invention.

FIGS. 7A, 7B, and 7C are diagrams showing tables used for converting outputs of the hole elements 113Y, 114Y, and 115Y into distances. FIG. 7A is a first table showing a relationship between the output voltage of each hole element and a distance in a case where the south (S) pole is detected. FIG. 7B is a second table showing a relationship between the output voltage of each hole element and a distance in a case where the north (N) pole is detected. FIG. 7C is a third table showing a relationship between the output voltage of each hole element and a distance in a case where the inverted-north (N) pole is detected.

Figure 8:
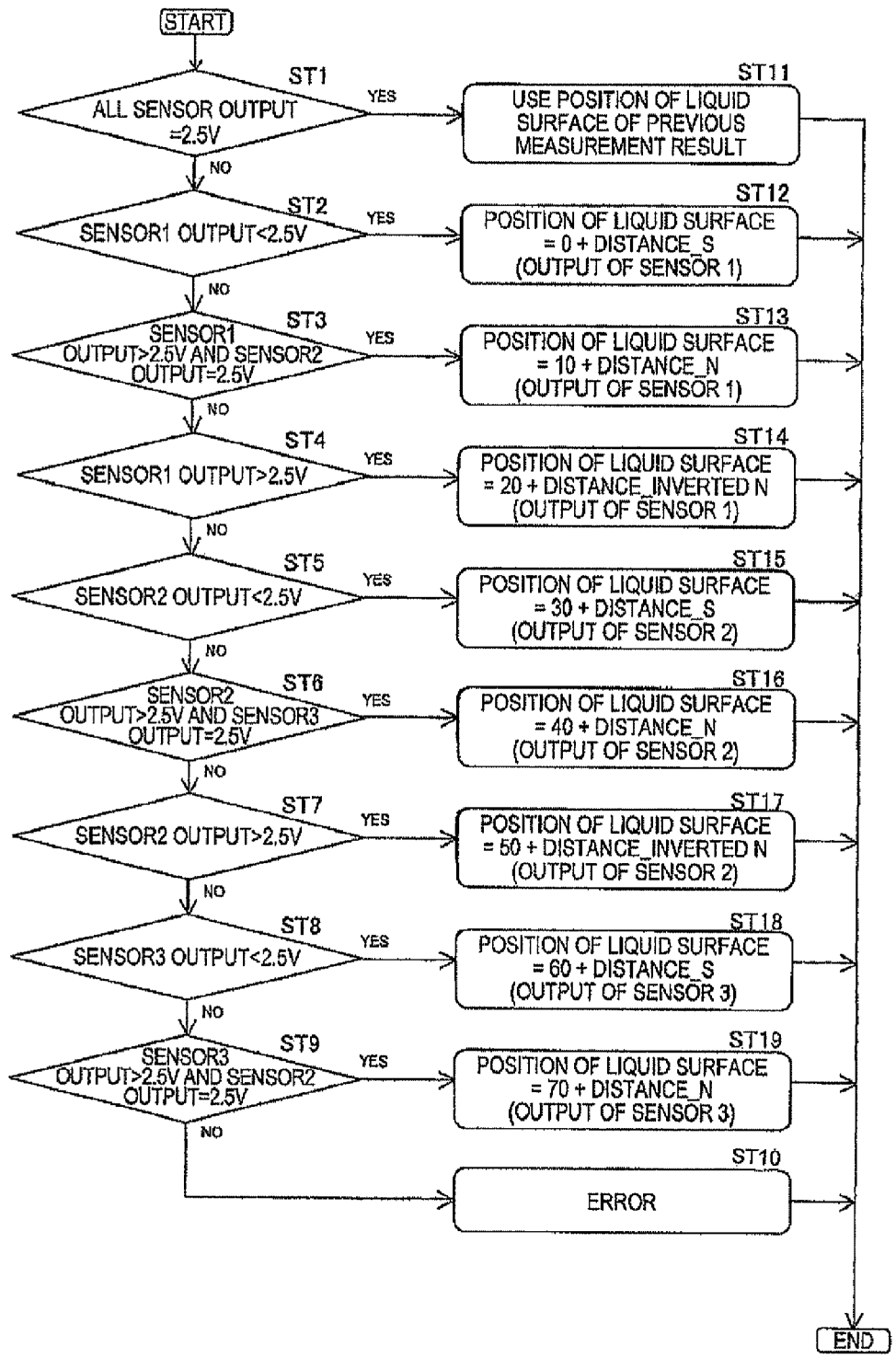
FIG. 8 is a flowchart for converting outputs of hole elements into a distance according to an embodiment of the invention.

FIG. 8 is a flowchart of a process for converting the outputs of the hole elements 113Y, 114Y, and 115Y into distances.

First, in Step 1, it is determined whether outputs of all the hole elements 113Y, 114Y, and 115Y are 2.5 V (ST1).

When the outputs of all the hole elements 113Y, 114Y, and 115Y are 2.5 V in Step 1, the result of the previous measurement is supposed to be used as the position of the liquid surface in Step 11 (ST11), and the process ends. On the other hand, when the outputs of all the hole elements 113Y, 114Y, and 115Y are not 2.5 V in Step 1, it is determined whether the output of the first hole element 113Y is lower than 2.5 V in Step 2 (ST2).

In Step 2, when the output of the first hole element 113Y is smaller than 2.5 V, the position of the liquid surface is set to a value that is acquired from the first table as a distance corresponding to the output of the first hole element 113Y (ST12), and the process ends. On the other hand, when the output of the first hole element 113Y is higher than 2.5 V in Step 2, in Step 3, it is determined whether the output of the second hole element 114Y is 2.5 V with the output of the first hole element 113Y higher than 2.5 V (ST3).

When the condition in Step 3 is satisfied, in Step 13, the position of the liquid surface is set as a value acquired from adding 10 mm to a value acquired from the second table as a distance corresponding to the output of the first hole element 113Y (ST13), and the process ends. On the other hand, when the condition in Step 3 is not satisfied, in Step 4, it is determined whether the output of the first hole element 113Y is higher than 2.5 V (ST4).

When the condition in Step 4 is satisfied, in Step 14, the position of the liquid surface is set as a value acquired from adding 20 mm to a value acquired from the third table as a distance corresponding to the output of the first hole element 113Y (ST14), and the process ends. On the other hand, when the condition in Step 4 is not satisfied, in Step 5, it is determined whether the output of the second hole element 114Y is lower than 2.5 V (ST5).

When the condition in Step 5 is satisfied, in Step 15, the position of the liquid surface is set as a value acquired from adding 30 mm to a value acquired from the first table as a distance corresponding to the output of the second hole element 114Y (ST15), and the process ends. On the other hand, when the condition in Step 5 is not satisfied, in Step 6, it is determined whether the output of the third hole element 115Y is 2.5 V with the output of the second hole element 114Y higher than 2.5 V (ST6).

When the condition in Step 6 is satisfied, in Step 16, the position of the liquid surface is set as a value acquired from adding 40 mm to a value acquired from the second table as a distance corresponding to the output of the second hole element 114Y (ST16), and the process ends. On the other hand, when the condition in Step 16 is not satisfied, in Step 7, it is determined whether the output of the second hole element 114Y is higher than 2.5 V (ST7).

When the condition in Step 7 is satisfied, in Step 17, the position of the liquid surface is set as a value acquired from adding 50 mm to a value acquired from the third table as a distance corresponding to the output of the second hole element 114Y (ST17), and the process ends. On the other hand, when the condition in Step 7 is not satisfied, in Step 8, it is determined whether the output of the third hole element 115Y is lower than 2.5 V (ST8).

When the condition in Step 8 is satisfied, in Step 18, the position of the liquid surface is set as a value acquired from adding 60 mm to a value acquired from the first table as a distance corresponding to the output of the third hole element 115Y (ST18), and the process ends. On the other hand, when the condition in Step 8 is not satisfied, in Step 9, it is determined whether the output of the second hole element 114Y is 2.5 V with the output of the third hole element 115Y higher than 2.5 V (ST9).

When the condition in Step 9 is satisfied, in Step 19, the position of the liquid surface is set as a value acquired from adding 70 mm to a value acquired from the third table as a distance corresponding to the output of the third hole element 115Y (ST19), and the process ends. On the other hand, when the condition in Step 9 is not satisfied, in Step 10, an error is determined (ST10), and the process ends.

Figure 9:
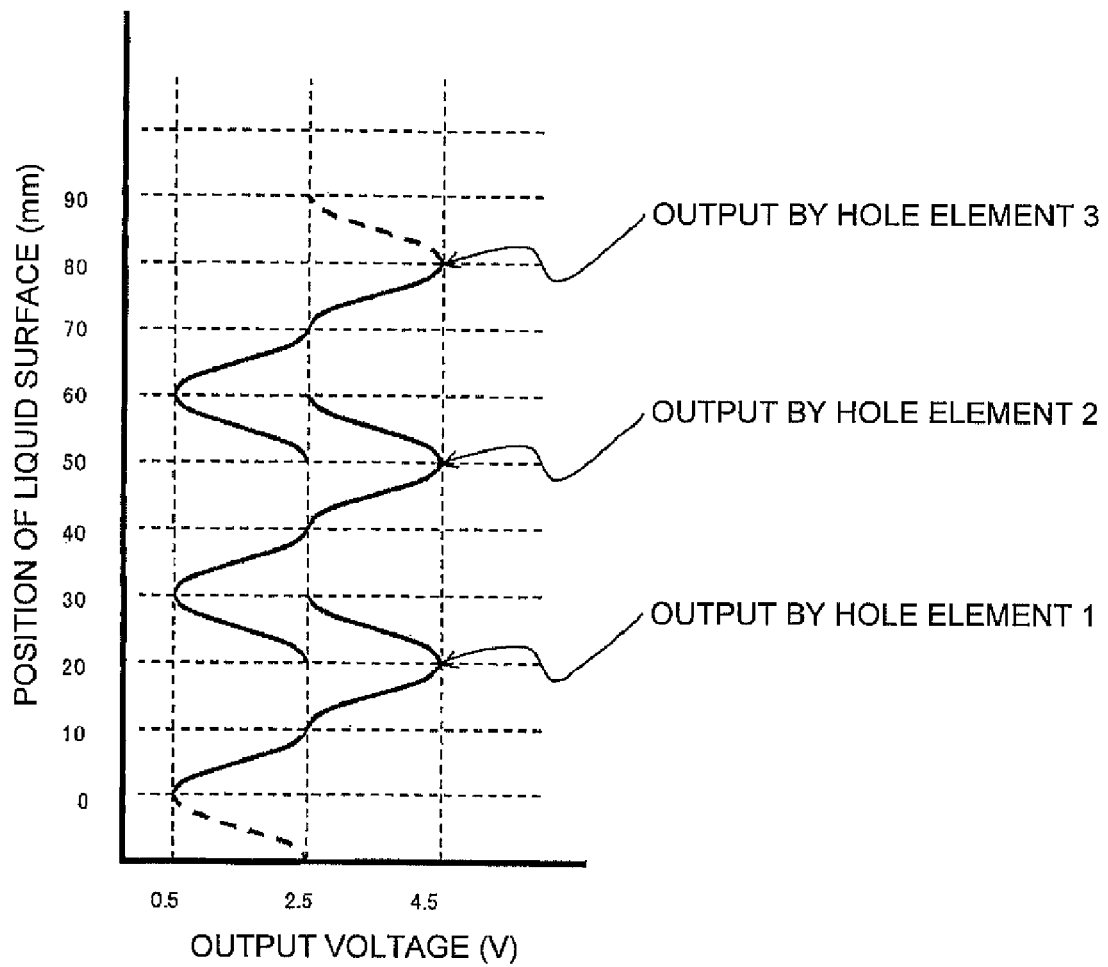
FIG. 9 is a diagram showing the result acquired from performing the process of the flowchart shown in FIG. 8.

FIG. 9 is a diagram showing the result acquired from performing the process of the flowchart shown in FIG. 8. As shown in FIG. 9, the position of the liquid surface corresponding to the outputs of the hole elements 113Y, 114Y, and 115Y can be acquired.

According to the above-described liquid measuring device 110Y, the number of components can be decreased and the costs can be suppressed to below. In addition, a long distance can be detected, and thereby halt of the system can be suppressed.

Figure 10:
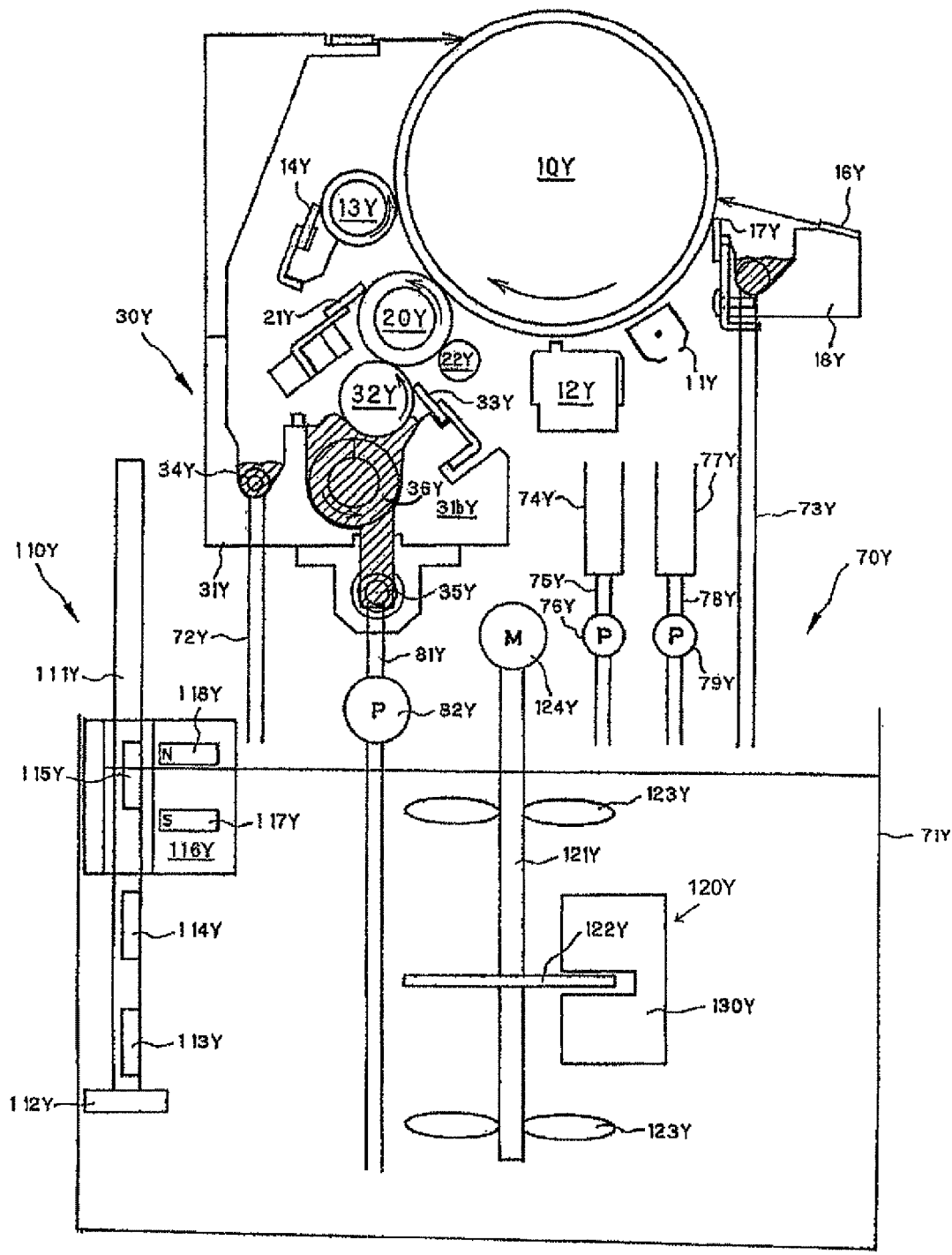
FIG. 10 is a diagram showing a liquid measuring device and a density detecting unit according to an embodiment of the invention.

As another embodiment of the invention, the density measuring device 120Y as shown in FIG. 10 may be provided.

As shown in FIG. 10, the density measuring device 120Y has an agitating propeller shaft 121Y, a transparent propeller 122Y as an example of a moving member, an agitating propeller 123Y as an example of an agitating member, a motor 124Y, and a density measuring unit 130Y.

The transparent propeller 122Y and the agitating propeller 123Y are disposed on a same shaft that is the agitating propeller shaft 121Y, and the agitating propeller shaft 121Y is a member that is rotated by the motor 124Y.

Figure 13:
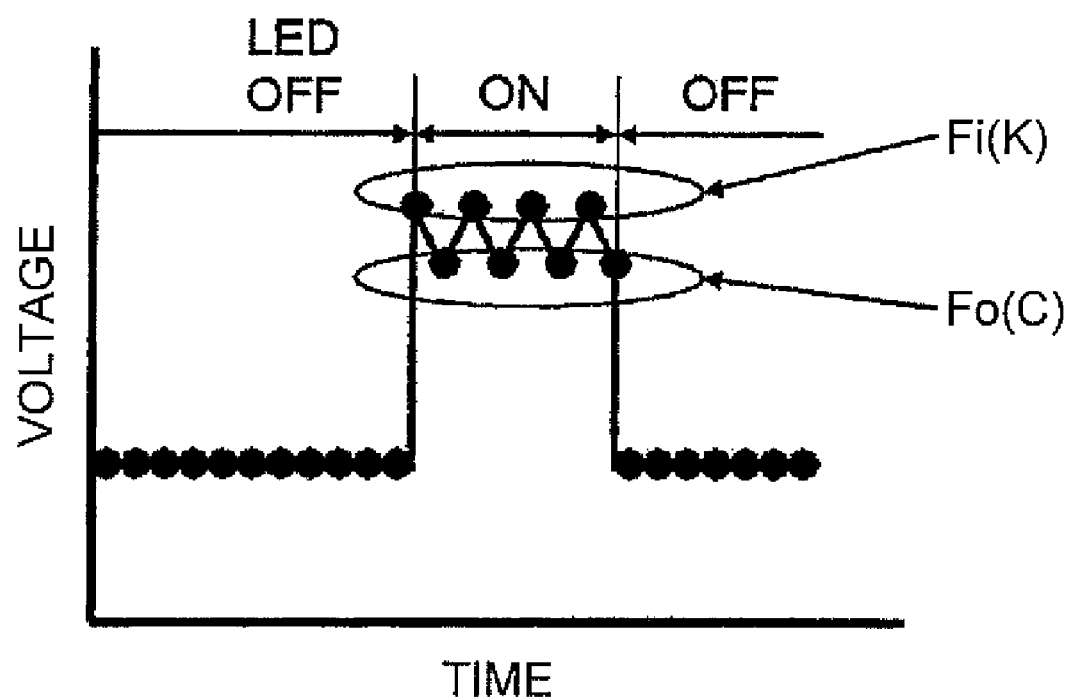
FIG. 13 is a diagram showing a change of a signal output from a density-measuring light receiving element according to an embodiment of the invention.
Figure 14A:
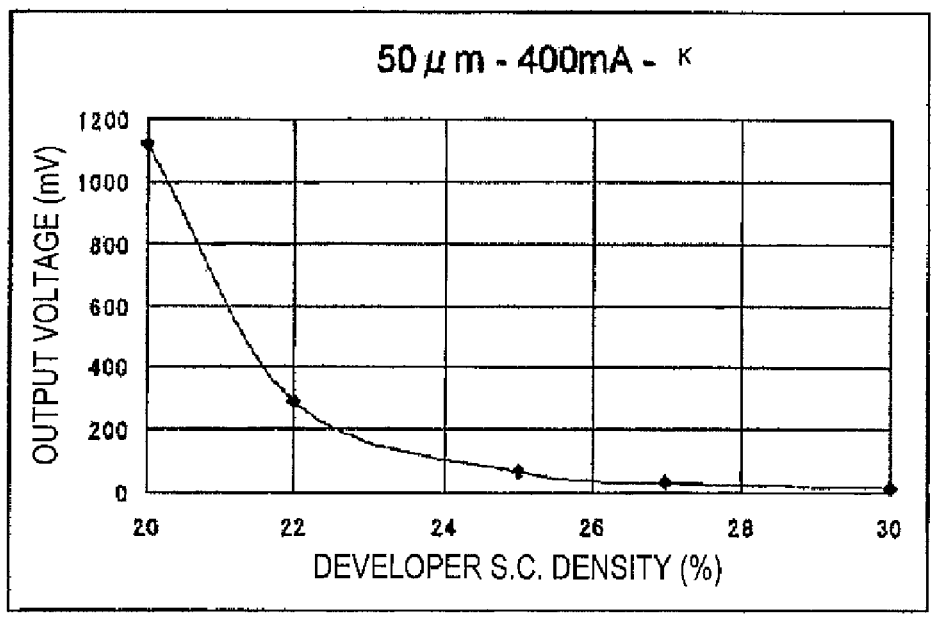
FIGS. 14A and 14B are graphs showing a relationship between an output voltage of a density-measuring light receiving element and the density of liquid developer according to an embodiment of the invention.
Figure 14B:
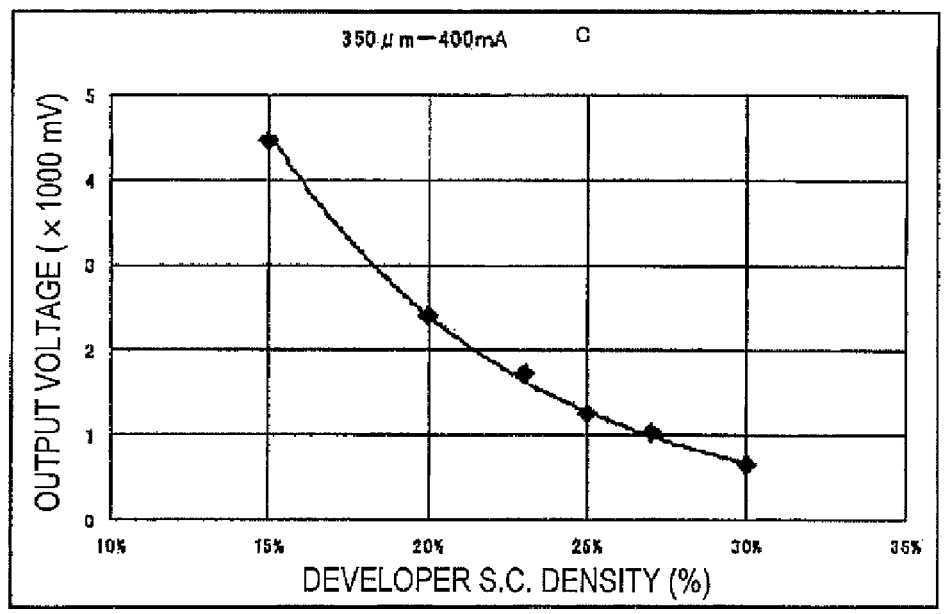
Figure 15:
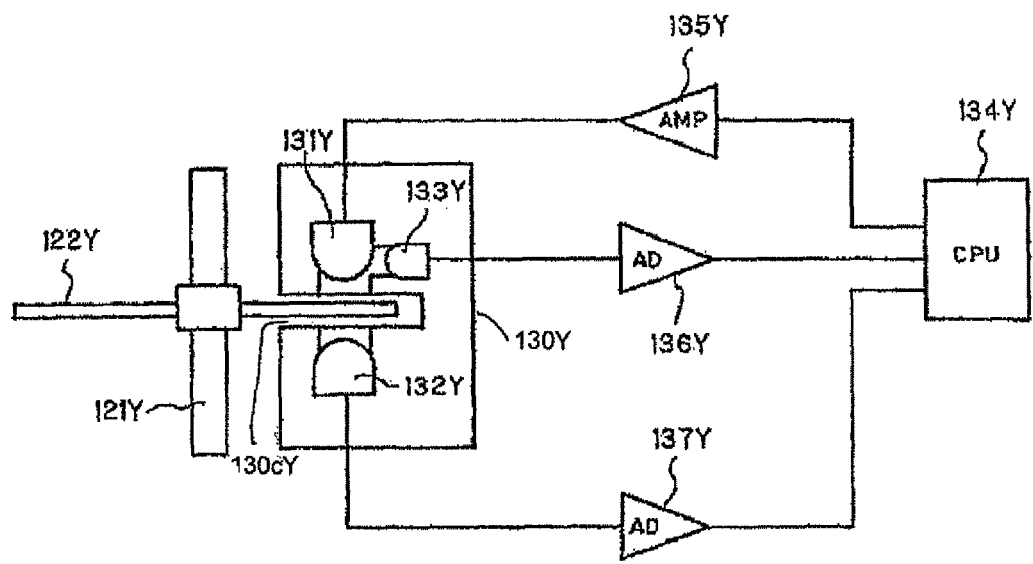
FIG. 15 is a system diagram of a transmission-type density measuring unit according to an embodiment of the invention.
Figure 16:
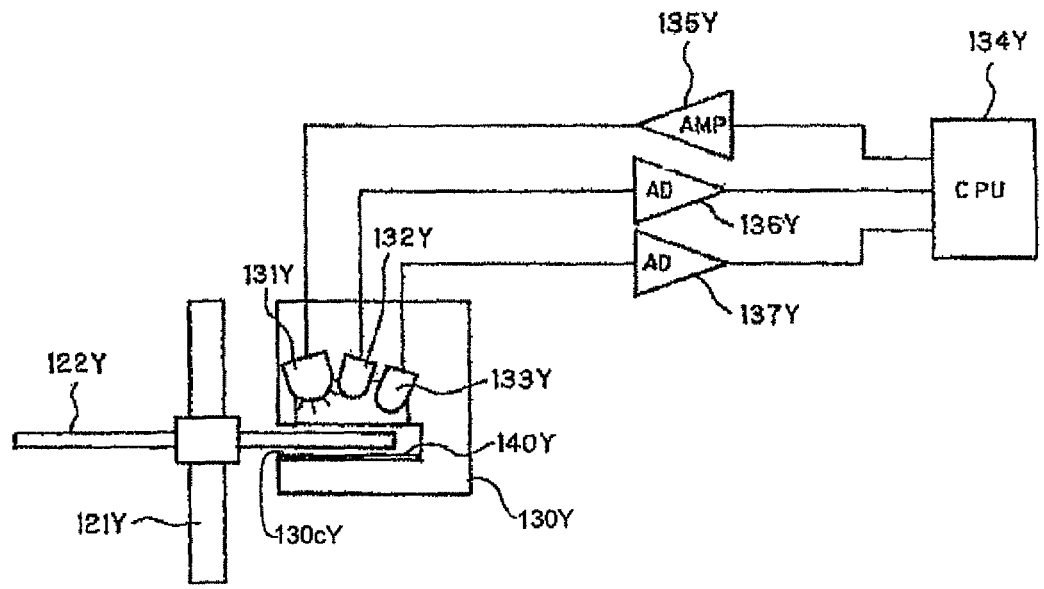
FIG. 16 is a system diagram of a reflection-type density measuring unit according to an embodiment of the invention.

Next, a density detecting method by using the density measuring unit 130Y and the transparent propeller 122Y will be described. FIG. 11 is an enlarged view of a part in the vicinity of the transparent propeller 122Y shown in FIG. 10. FIGS. 12A and 12B are enlarged views of a gap part. FIG. 13 is a diagram showing a change of a signal output from a density-measuring light receiving element 132Y. FIGS. 14A and 14B are graphs showing a relationship between the output voltage of the density-measuring light receiving element 132Y and the density of liquid developer. FIG. 15 is a system diagram of a transmission-type density measuring unit 130Y. FIG. 16 is a system diagram of a reflection-type density measuring unit 130Y.

As shown in FIG. 11, the transparent propeller 122Y is supported by the agitating propeller shaft 121Y and is formed of a member having a flat plate shape such as a rectangle that can be rotatable. The transparent propeller 122Y has a structure for intermittently passing a gap 130cY between first and second members 130aY and 130bY of the density measuring unit 130Y. The first member 130aY or the second member 130bY can be moved, and thus a distance of the gap 130cY can be changed. The distance of the gap 130cY may be changed in accordance with the color of the liquid developer.

Next, a simple principle of the density detecting method will be described. FIGS. 12A and 12B are enlarged views of the gap 130cY. FIG. 13 is a diagram showing a change of a signal output from the density-measuring light receiving element 132Y. As shown in FIG. 12A, when the transparent propeller 122Y is not positioned between a light emitting diode (LED) 131Y and the density-measuring light receiving element 132Y, the density-measuring light receiving element 132Y outputs a signal having a smaller value Fo between graphs shown in FIG. 13. As shown in FIG. 12B, when the transparent propeller 122Y is positioned between the light emitting diode (LED) 131Y and the density-measuring light receiving element 132Y, the density-measuring light receiving element 132Y outputs a signal having a larger value Fi between graphs shown in FIG. 13. In this embodiment, a value for acquiring a density value is selected for each color. For example, for black, a density value is acquired by averaging values Fl, and for cyan, a density value is acquired by averaging values Fo.

FIGS. 14A and 14B are graphs showing a relationship between the output voltage of the density-measuring light receiving element 132Y and the density of liquid developer. FIG. 14A shows a relationship between the output voltage of the density-measuring light receiving element 132Y and the density of liquid developer for black. In addition, FIG. 14B shows a relationship between the output voltage of the density-measuring light receiving element 132Y and the density of liquid developer for cyan.

In the transmission-type density measuring unit 130Y as shown in FIG. 15, a light emitting diode (LED) 131Y as an example of the density measuring member and the density-measuring light receiving element 132Y are disposed to face each other with a gap 130cY interposed therebetween. On the light emitting diode (LED) 131Y side, an emission intensity-measuring light receiving element 133Y as a second light receiving element is disposed.

Under such a structure, light emitted from the light emitting diode (LED) 131Y has a light path formed through liquid developer on the light emitting diode (LED) 131Y side relative to the transparent propeller 122Y, the transparent propeller 122Y, and liquid developer on the density-measuring light receiving element 132Y side relative to the transparent propeller 122Y to the density-measuring light receiving element 132Y and a light path reaching the emission intensity measuring light receiving element 133Y not through the transparent propeller 122Y or the liquid developer.

The light emitting diode (LED) 131Y, the density-measuring light receiving element 132Y and the emission intensity-measuring light receiving element 133Y are connected to a CPU 134Y. The light emitting diode (LED) 131Y is connected to the CPU 134Y through an amplifier 135Y. In addition, the density-measuring light receiving element 132Y is connected to the CPU 134Y through a first A/D converter 137Y. The emission intensity-measuring light receiving element 133Y is connected to the CPU 134Y through a second AID converter 136Y.

In the reflection-type density measuring unit 130Y as shown in FIG. 16, on one side of a gap 130cY, the light emitting diode (LED) 131Y, the density-measuring light receiving element 132Y, and the emission intensity-measuring light receiving element 133Y are disposed. In addition, on the other side of the gap 130cY, a reflective film 140Y is disposed.

Under such a structure, light emitted from the light emitting diode (LED) 131Y has a light path formed through liquid developer on the light emitting diode (LED) 131Y side relative to the transparent propeller 122Y, the transparent propeller 122Y, and liquid developer on the reflective film 140Y side, reflected from the reflective film 140Y, and then through liquid developer on the reflective film 140Y side, the transparent propeller 122Y, liquid developer on the density-measuring light receiving element 132Y side relative to the transparent propeller 122Y to the density-measuring light receiving element 132Y and a light path formed through the liquid developer on the light emitting diode (LED) 131Y side relative to the transparent propeller 122Y to the emission intensity-measuring light receiving element 133Y.

The light emitting diode (LED) 131Y, the density-measuring light receiving element 132Y and the emission intensity-measuring light receiving element 133Y are connected to the CPU 134Y. The light emitting diode (LED) 131Y is connected to the CPU 134Y through an amplifier 135Y. In addition, the density-measuring light receiving element 132Y is connected to the CPU 134Y through a first A/D converter 136Y. The emission intensity-measuring light receiving element 133Y is connected to the CPU 134Y through a second A/D converter 137Y.

Figure 17:
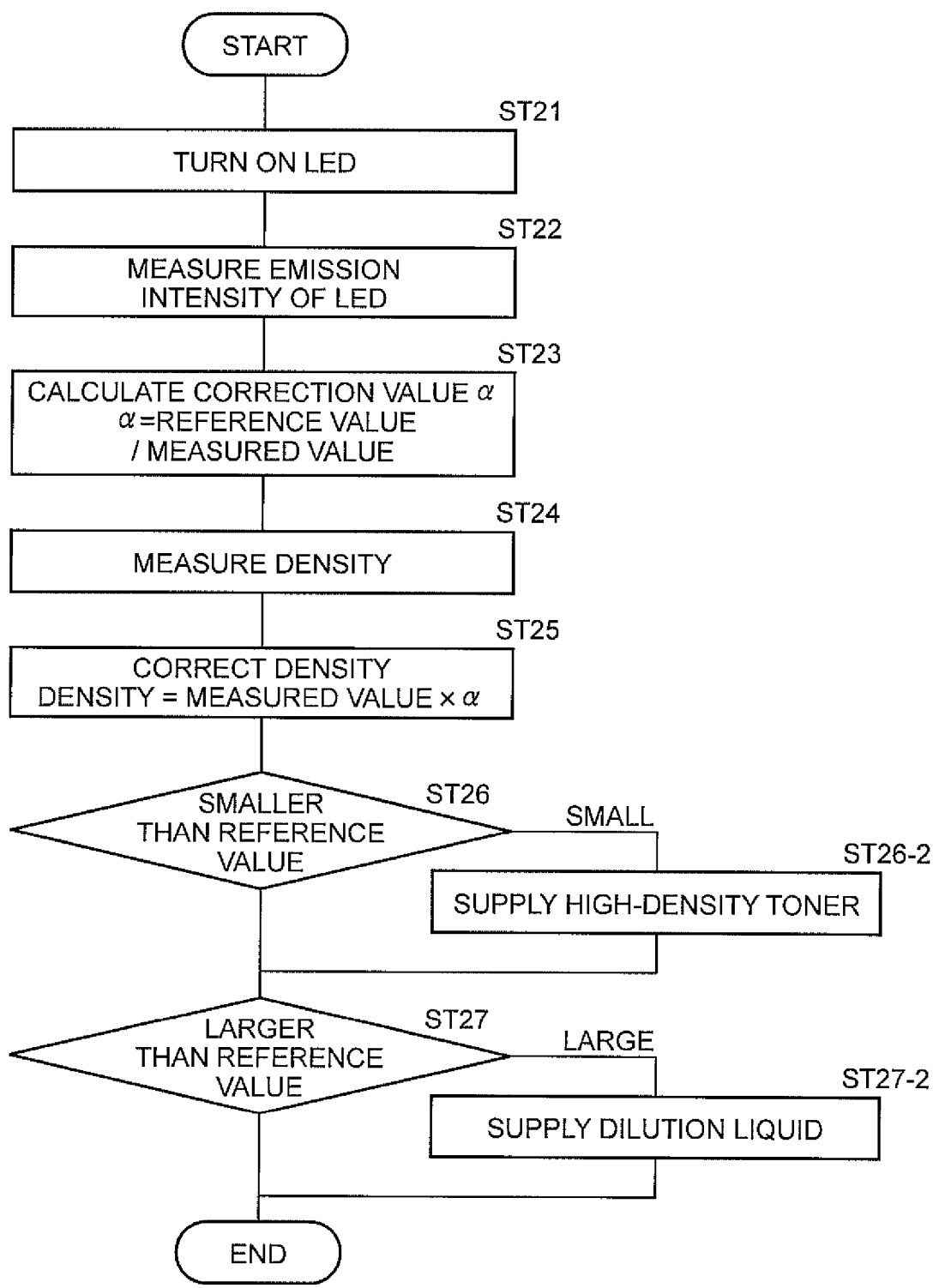
FIG. 17 is a flowchart for showing a detection process of a density measuring device according to an embodiment of the invention.

Next, a detection method using the above-described density measuring device 120Y will be described. FIG. 17 is a flowchart of a detection process of the density measuring device 120Y.

First, in Step 21, the light emitting diode (LED) 131Y is turned on (ST21). Subsequently, in Step 22, the light intensity of the light emitting diode (LED) 131Y is measured by using the emission intensity-measuring light receiving element 133Y (ST22).

Next, in Step 23, a correction value α is calculated (ST23). The correction value α is acquired by comparing a measured value measured by the emission intensity-measuring light receiving element 133Y with a reference value of the light emitting diode (LED) 131Y.

Next, In Step 24, the density is measured by using the density-measuring light receiving element 132Y (ST24).

Subsequently, in Step 25, the density of the liquid developer is acquired by performing density correction by using the CPU 134Y (ST25). The density of the liquid developer is acquired by multiplying the measured value that has been measured by the density-measuring light receiving element 132Y in Step 24 by the correction value a acquired in Step 23.

Next, in Step 26, it is determined whether the density of the liquid developer is smaller than a density reference value stored in advance (ST26). When the density of the liquid developer is determined to be smaller than the density reference value, high-density developer is supplied (ST26-2) from the developer tank 74Y to the liquid developer storing unit 71Y through a developer supplying path 75Y and a developer pump 76Y.

On the other hand, when the density of the liquid developer is determined not to be smaller than the density reference value in Step 26, it is determined whether the density of the liquid developer is larger than the density reference value stored in advance in Step 27 (ST27). When the density of the liquid developer is determined to be larger than the density reference value, the carrier liquid is supplied (ST27-2) from the carrier liquid tank 77Y to the liquid developer storing unit 71Y through the carrier liquid supplying path 78Y and the carrier liquid pump 79Y.

By controlling the density of the liquid developer as described above, the density of the liquid developer inside the liquid developer storing unit 71Y becomes approximately constant.

Next, control of the developer pump 76Y and the carrier liquid pump 79Y will be described. The control amounts of the developer pump 76Y and the carrier liquid pump 79Y are controlled by the amount of toner contained in the liquid developer or the amount of shortage of the carrier liquid.

First, the amount of toner contained in the liquid developer and the amount of the carrier liquid are calculated by using the liquid measuring device 110Y and the density measuring device 120Y shown in FIG. 10. Then, shortages of the amount of toner contained in the liquid developer and the amount of the carrier liquid for object values that are stored in advance are calculated.

Figure 18:
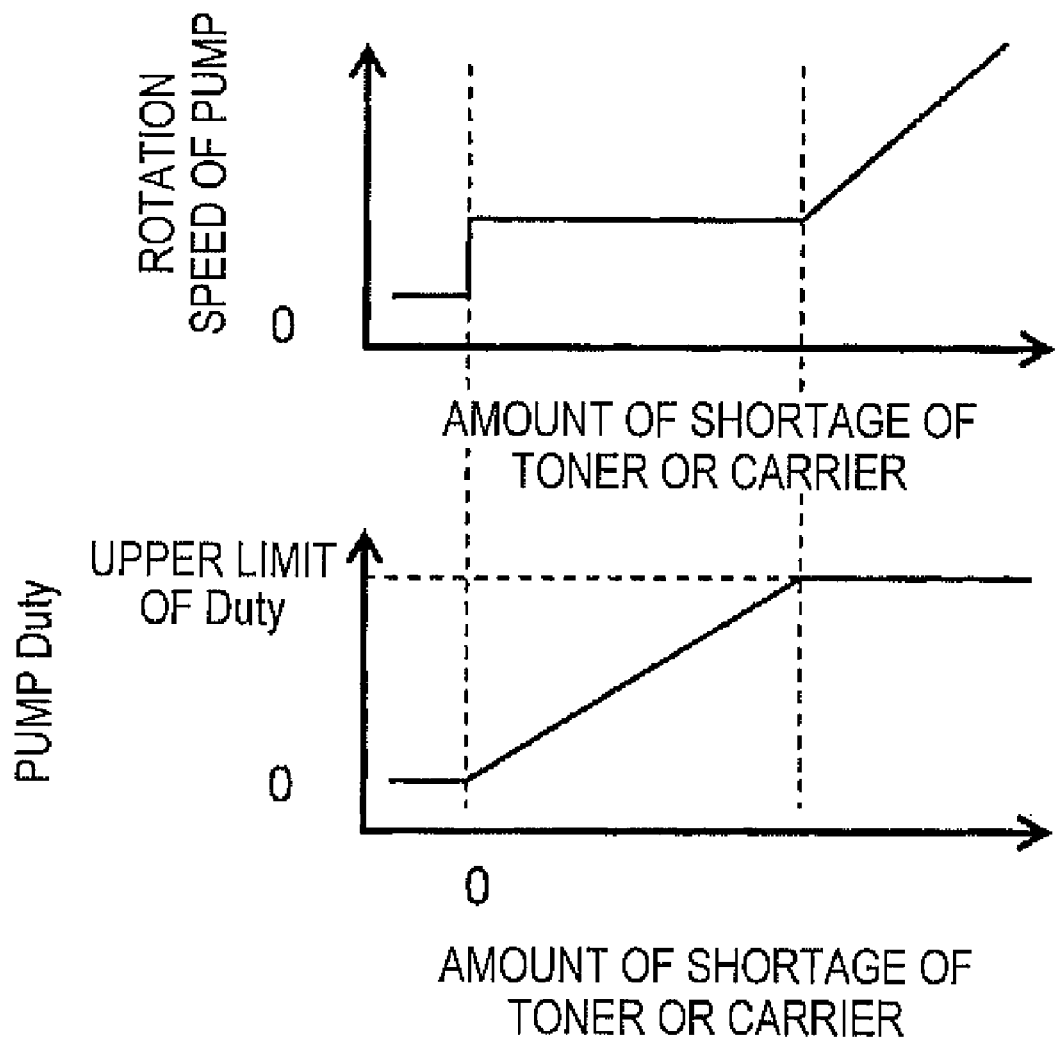
FIG. 18 is a diagram showing rotation speeds and duty values of a developer pump and a carrier liquid pump for shortages of the amount of toner or the amount of the carrier liquid according to an embodiment of the invention.

FIG. 18 is a diagram showing rotation speeds and duty values of the developer pump 76Y and the carrier liquid pump 79Y for shortages of the amount of toner or the amount of the carrier liquid. As shown in FIG. 18, the developer pump 76Y and the carrier liquid pump 79Y have constant rotation speeds up to the upper limits of the duty values, and the duty values thereof are changed in accordance with the amount of shortages. After the upper limits of the duty values are reached, the numbers of rotations are increased in accordance with the amounts of shortages.

Figure 19:
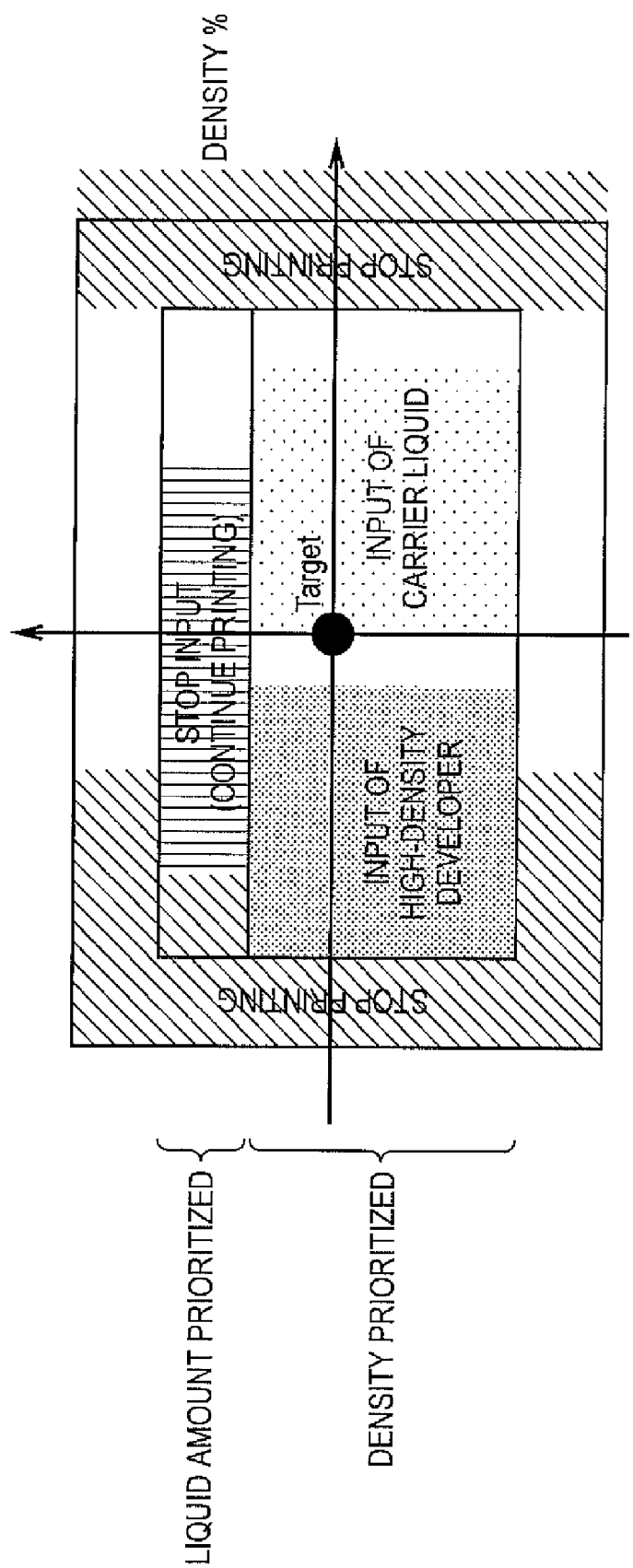
FIG. 19 is a diagram showing priorities of control for the amount and density of the liquid developer inside a liquid developer storing unit according to an embodiment of the invention.

Next, a control process for priority of control in a printing state will be described. FIG. 19 is a diagram showing priorities of control for the amount and density of the liquid developer inside the liquid developer storing unit 71Y.

As shown in FIG. 19, there are a liquid-level prioritizing mode in which the developer collecting and supplying device 70Y is controlled based on the result of measurement of the liquid measuring device 110Y and a density prioritizing mode in which the developer collecting and supplying device 70Y is controlled based on the result of measurement of the density measuring device 120Y. In addition, when the liquid level measured by the liquid measuring device 110Y is higher than a first predetermined level, the liquid-level prioritizing mode is set, and liquid input is prohibited.

In addition, when the density measured by the density measuring device 120Y is higher than a first predetermined level or lower than a second predetermined level that is set to be lower than the first predetermined level, printing is stopped. On the other hand, when the density measured by the density measuring device 120Y is lower than a first predetermined density and higher than a second predetermined density or when the liquid level measured by the liquid measuring device 110Y is lower than the first predetermined liquid level and higher than the second predetermined liquid level, the density prioritizing mode is set, and the carrier liquid or the high-density developer is input in accordance with the density and the liquid level.

For example, up to a liquid amount of a certain degree, the density is prioritized. Thus, when the density is high, the carrier liquid is input from the carrier liquid tank 77Y to the liquid developer storing unit 71Y. On the other hand, when the density is low, high-density developer is input from the developer tank 74Y to the liquid developer storing unit 71Y. In a case where the liquid amount is prioritized, when the liquid amount is large and exceeds a predetermined amount, the liquid amount is prioritized, and thus input of the carrier liquid and the high density developer is stopped regardless of the density. In addition, the printing is continued. When the density is larger than the first predetermined density or is lower than the second predetermined density that is set lower than the first predetermined density, or when the liquid amount is beyond a specific range, the printing is stopped.

In addition, the speeds of the developer compressing roller 22Y and the developer supplying roller 32Y may be controlled in accordance with the detected density so as to control the density of the developer in the developing nip.

Figure 20:
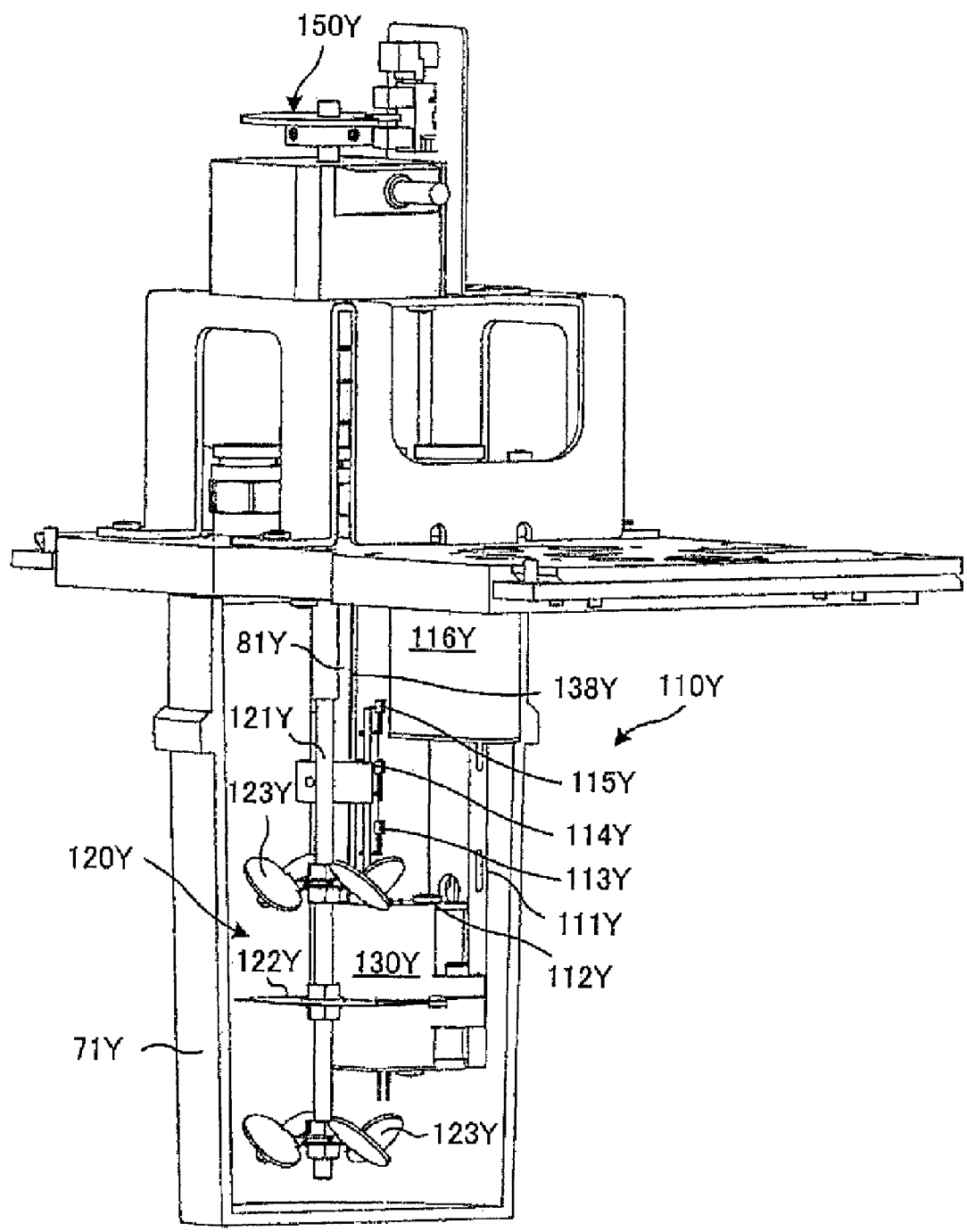
FIG. 20 is a perspective view of a liquid developer storing unit according to another embodiment of the invention.
Figure 21:
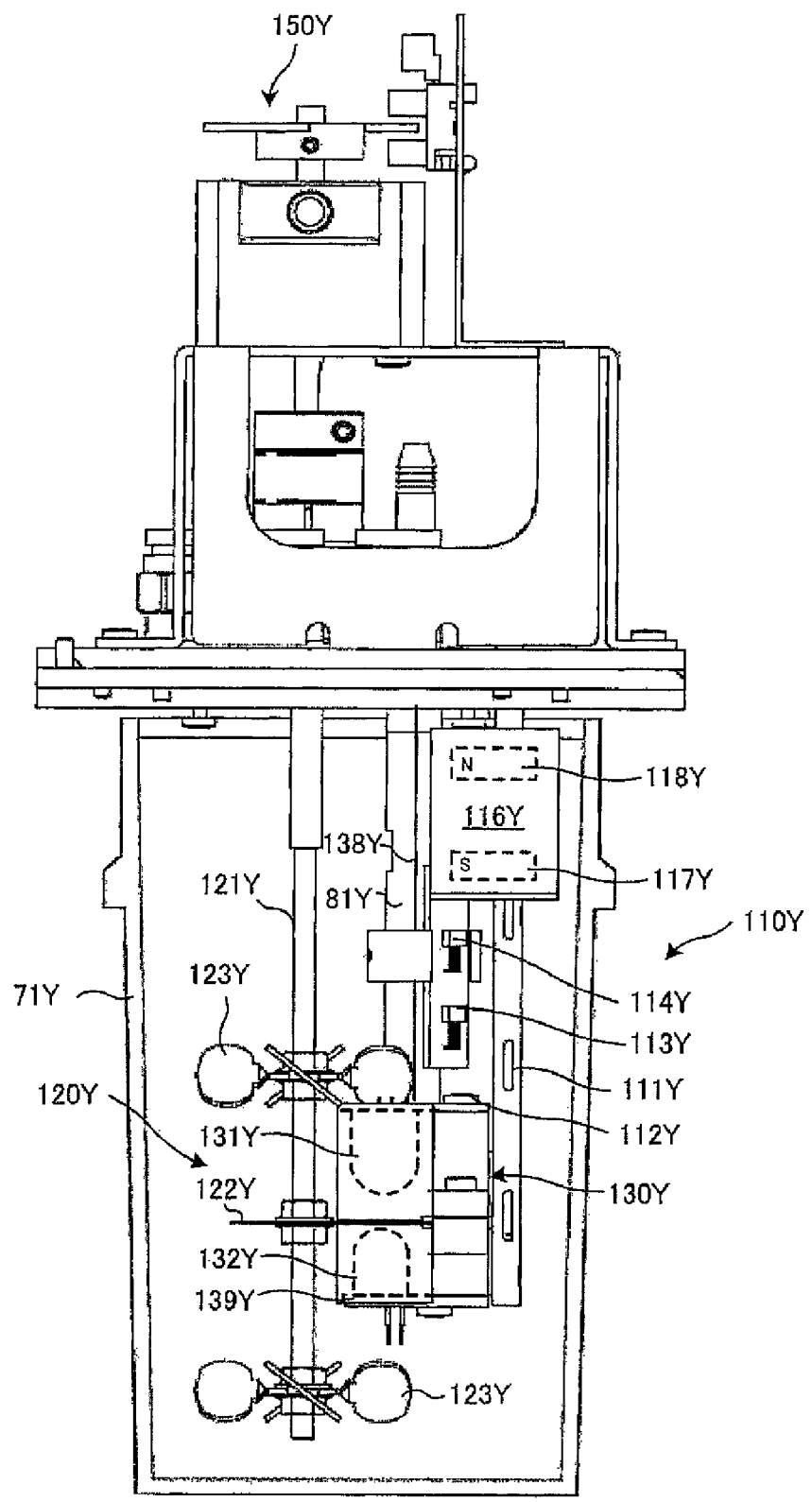
FIG. 21 is a cross-section view of a liquid developer storing unit according to another embodiment of the invention.
Figure 22:
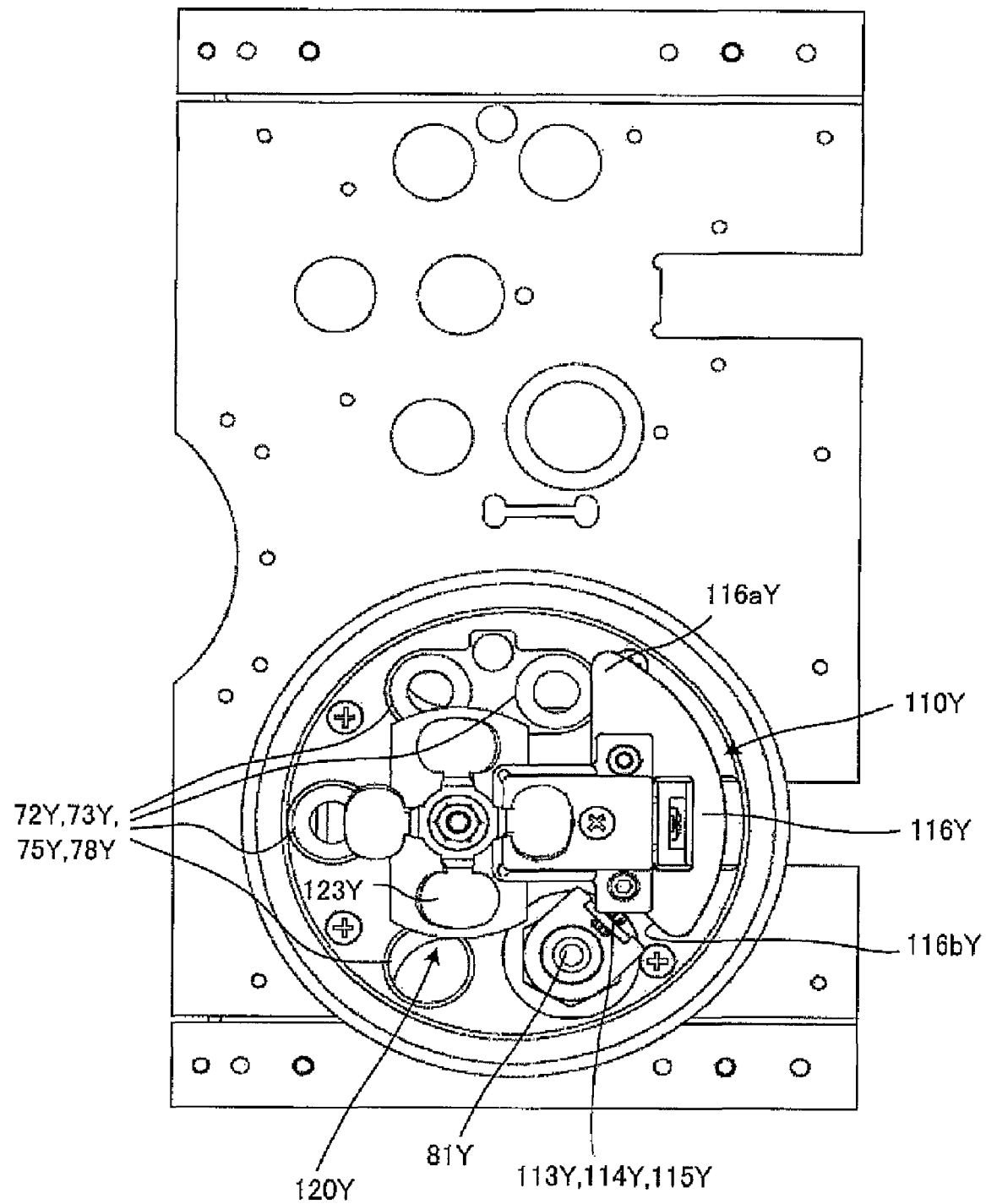
FIG. 22 is a diagram of a liquid developer storing unit according to another embodiment of the invention, viewed from the lower side.
Figure 23:
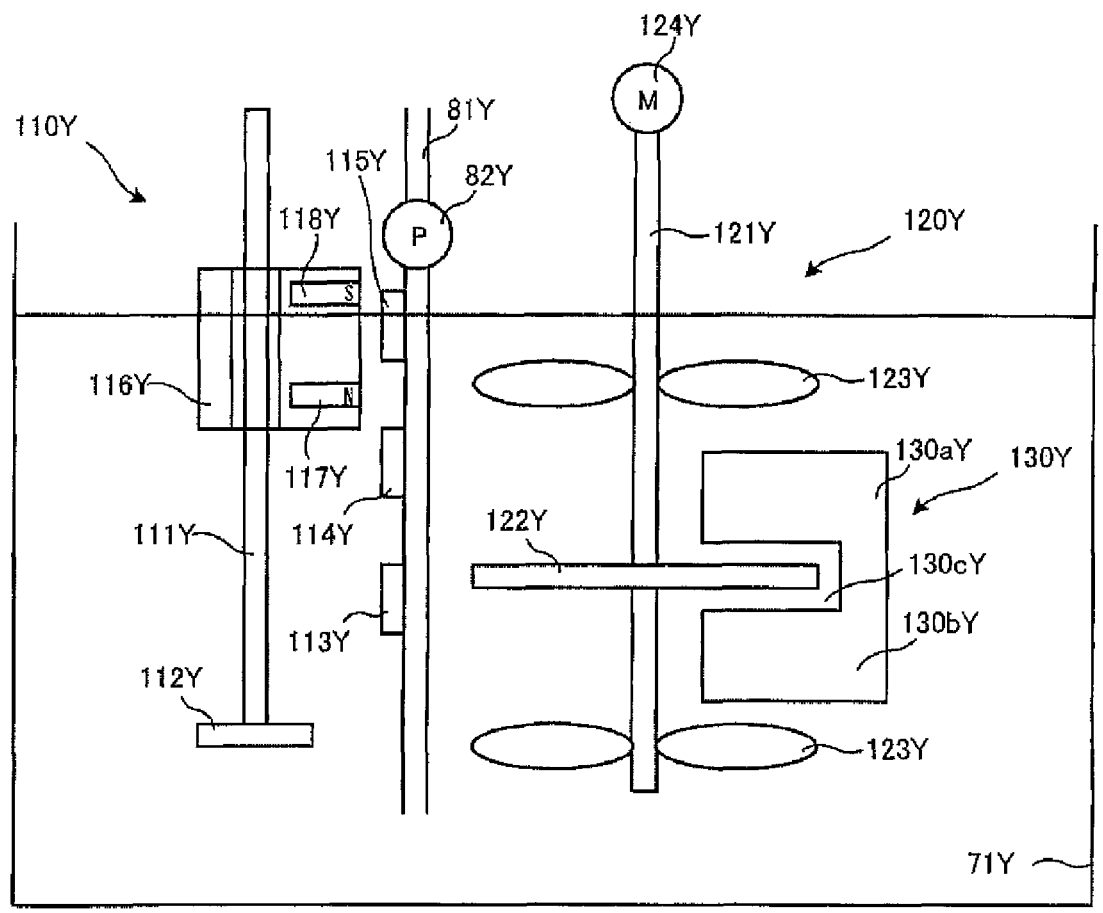
FIG. 23 is schematic diagram of a liquid developer storing unit according to another embodiment of the invention.

FIGS. 20 to 23 are diagrams showing a liquid measuring device 110Y and a density measuring device 120Y, located inside the liquid developer storing unit 71Y, according to another embodiment of the invention. FIG. 20 is a perspective view of a liquid developer storing unit 71Y according to another embodiment of the invention. FIG. 21 is a cross-section view of a liquid developer storing unit 71Y according to another embodiment of the invention. FIG. 22 is a diagram of a liquid developer storing unit 71Y according to another embodiment of the invention, viewed from the lower side. FIG. 23 is a schematic diagram of a liquid developer storing unit 71Y according to another embodiment of the invention. The liquid measuring device 110Y and the density measuring device 120Y, located inside the liquid developer storing unit 71Y measure the liquid level and the density of the liquid developer, similarly to the diagram shown in FIG. 10. In this embodiment, the first hole element 113Y, the second hole element 114Y, and the third hole element 115Y are disposed in the developer supplying path 81Y used for supplying the liquid developer from the liquid developer storing unit 71Y to a supply unit 31bY of the developer container 31Y.

First, the liquid measuring device 110Y as a liquid level sensor will be described. The liquid measuring device 110Y has a float supporting member 111Y, a regulating member 112Y, the first hole element 113Y, the second hole element 114Y, and the third hole element 115Y that are examples of proportional output-type hole elements, a float 116Y as an example of a floating member, and first and second magnetic field generators 117Y and 118Y.

The float supporting member 111Y supports the float 116Y to be movable from a position on the liquid surface inside the liquid developer storing unit 71Y of yellow to a measurable position below the liquid surface. The regulating member 112Y is disposed in the density measuring unit 130Y of the density measuring device 120Y and prevents interferences of the float 116Y and the density measuring unit 130Y.

The first hole element 113Y, the second hole element 114Y, and the third hole element 115Y are sequentially disposed from the lower side with a predetermined distance apart from the developer supplying path 81Y through a bracket or the like.

The first hole element 113Y, the second hole element 114Y, and the third hole element 115Y are formed of proportional output-type hole members of which output voltage changes in accordance with magnetic flux density. In this embodiment, the distance between the hole elements is set to 30 mm.

The float 116Y is a member that is movable relative to the float supporting member 111Y by floating on the liquid surface in accordance with the position of the liquid surface. On the lower side of the float 116Y, the first magnetic field generator 117Y is disposed, and the second magnetic field generator 118Y is disposed on the upper side thereof to be a predetermined distance apart from the first magnetic field generator 117Y. The first magnetic field generator 117Y and the second magnetic field generator 118Y are disposed to be moved in accordance with movement of the float 116Y while facing the hole elements 113Y, 114Y, and 115Y. The first magnetic field generator 117Y and the second magnetic field generator 118Y are disposed to have the north (N) pole and the south (S) pole disposed on opposite sides. In this embodiment, the first magnetic field generator 117Y is configured to have its south (S) pole facing the first direction so as to face the hole elements 113Y, 114Y, and 115Y, and the second magnetic field generator 117Y is configured to have its north (N) pole facing the first direction so as to face the hole elements 113Y, 114Y, and 115Y. The magnetic field generators 117Y and 118Y having a diameter of 5 mm, a length of 6 mm, and 4000 Gauss are disposed to be spaced apart by 20 mm.

When the liquid surface of the liquid developer changes, the float 116Y is moved, and accordingly, distances between the first and second magnetic field generators 117Y and 118Y and the hole elements 113Y, 114Y, and 115Y are changed. In accordance with the changes in the distances, magnetic fields detected by the hole elements 113Y, 114Y, and 115Y change, and thus, it is possible to acquire the liquid level based on the detected values of the hole elements 113Y, 114Y, and 115Y.

The density measuring device 120Y has an agitating propeller shaft 121Y, a transparent propeller 122Y as an example of a moving member, an agitating propeller 123Y as an example of an agitating member, and a density measuring unit 130Y. The transparent propeller 122Y and the agitating propeller 123Y are disposed on a same shaft that is the agitating propeller shaft 121Y, and the agitating propeller shaft 121Y is a member that is rotated by a motor 124Y.

Since the structure of the density measuring unit 130Y is almost the same as that shown in FIGS. 11 and 12, a description of a same element will be omitted here.

The density measuring unit 130Y has a case formed of an insulating member such as plastic. The case has a gap 130cY, and the transparent propeller 122Y is supported by the agitating propeller shaft 121Y and is formed of a member having a flat plate shape such as a rectangle that can be rotated. The transparent propeller 122Y has a structure for intermittently passing the gap 130cY between first and second members 130aY and 130bY of the density measuring unit 130Y. The first member 130aY or the second member 130bY can be moved, and thus a distance of the gap 130cY can be changed. The distance of the gap 130cY may be changed in accordance with the color of the liquid developer.

The density measuring unit 130Y has a light emitting diode (LED) 131Y, a density-measuring light receiving element 132Y, a an emission intensity-measuring light receiving element 133Y, and the like, and wirings 138Y thereof are disposed in the developer supplying path 81Y. The density-measuring light receiving element 132Y, the emission intensity-measuring light receiving element 133Y, and the like are supported by a metal plate 139Y that is electrically floating, and accordingly, it is possible to reduce electrical influence on the density measuring unit 130Y.

In addition, the liquid measuring device 110Y and the density measuring device 120Y have a position adjusting mechanism 150Y that can adjust a height on the whole. Thus, the whole position can be adjusted, and accordingly, the degree of freedom for design increases.

As shown in FIG. 22, when this embodiment is viewed from the lower side, the agitating propeller 123Y is rotated in the clockwise direction and is disposed to be overlapped with at least one of openings of the developing unit collecting path 72Y, the image carrier collecting path 73Y, the developer supplying path 75Y, and the carrier liquid supplying path 78Y. Accordingly, newly collected or supplied liquid developer can be agitated in a speedy manner.

In addition, the float 116Y has a fan-shaped section, and an end part 116aY of the float 116Y opposite to the hole elements 113Y, 114Y, and 115Y has a rounded acute-angled shape so as to enable the liquid developer to flow in an easy manner. In addition, a face 116bY of the float 116Y opposite to the end part 116aY faces the hole elements 113Y, 114Y, and 115Y. Accordingly, the flow of the liquid developer is reduced, and the precision of the hole elements 113Y, 114Y, and 115Y is improved.

Figure 24:
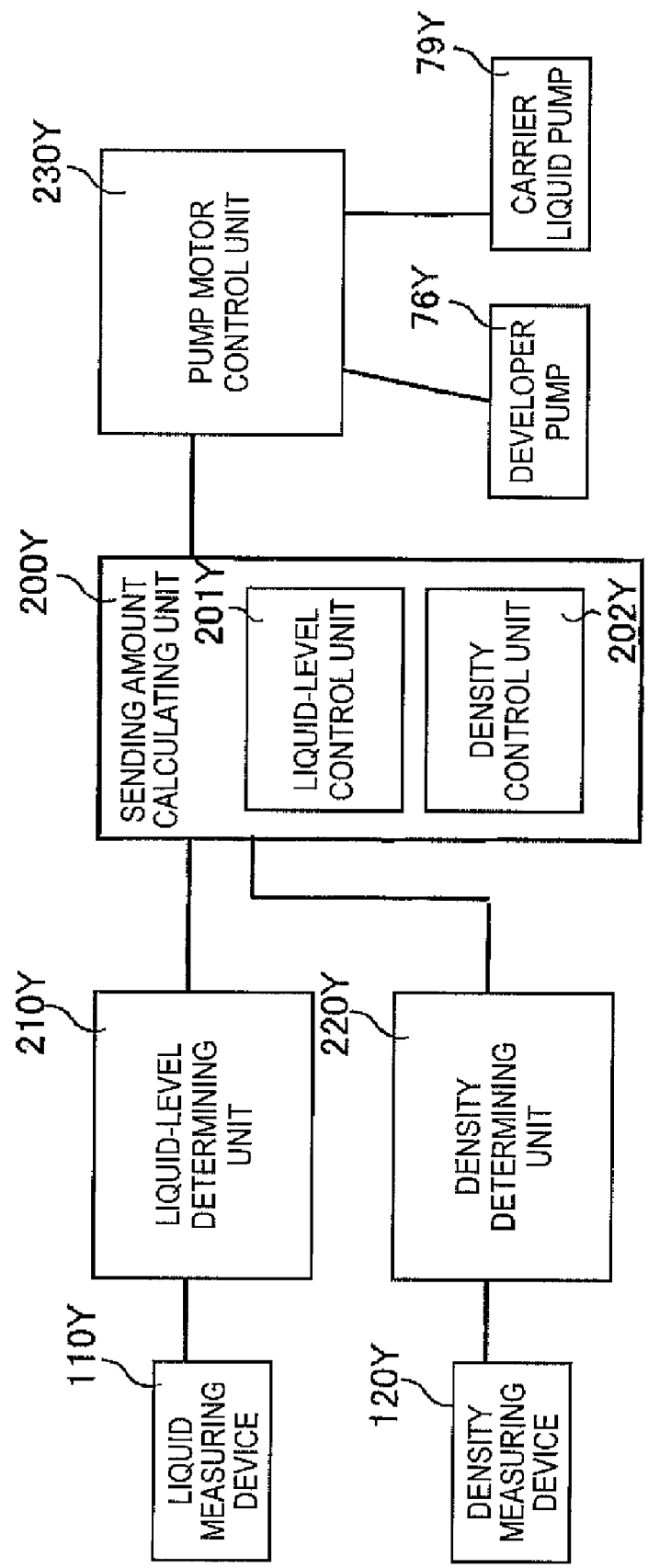
FIG. 24 is a block diagram showing a relationship of a liquid measuring device, a density measuring device in a developer collecting and supplying device according to an embodiment of the invention.

FIG. 24 is a block diagram showing a relationship of the liquid measuring device 110Y, the density measuring device 120Y, and the developer collecting and supplying device 70Y according to an embodiment of the invention.

A liquid level determining unit 210Y determines whether the liquid level measured by the liquid measuring device 110Y is higher than a predetermined level, When the liquid level determining unit 210Y determines that the liquid level measured by the liquid measuring device 110Y is higher than the predetermined level, a liquid sending amount calculating unit 200Y sets the liquid amount prioritizing mode to be used and outputs a signal from a liquid-level control unit 201Y to a pump motor control unit 230Y so as to prohibit input of the liquid developer. The pump motor control unit 230Y prohibits operation of pump motors such as the developer pump 76Y, the carrier liquid pump 79Y, and the like so as to prohibit input of the liquid developer. Accordingly, an overflow and the like can be eliminated.

In addition, it is determined whether the density measured by the density measuring device 120Y is higher or lower than a first or second predetermined density by a density determining unit 220Y. When the density determining unit 220Y determines that the density measured by the density measuring device 120Y is higher than the first predetermined density or is lower than the second predetermined density that is lower than the first predetermined density, the density determining unit 220Y sets the density prioritizing mode to be used and stops printing by using a density control unit 202Y. Accordingly, an image is not formed with a deteriorated image quality.

As described above, the image forming apparatus according to an embodiment of the invention has a liquid-amount prioritizing mode in which the developer collecting and supplying device 70Y is controlled based on the result of measurement of the liquid measuring device 110Y and a density prioritizing mode in which the developer collecting and supplying device 70Y is controlled based on the result of measurement of the density measuring device 120Y. In addition, the sending amount calculating unit 200Y as a selection unit selects one between the liquid-amount prioritizing mode and the density prioritizing mode. Accordingly, the image forming apparatus can be controlled based on the liquid amount and density of the liquid developer, and thereby an image with excellent image quality can be formed in accordance with the state of the liquid developer.

In addition, the liquid developer storing apparatus according to an embodiment of the invention is configured by the liquid developer storing unit 71Y, the liquid measuring device 110Y, the density measuring device 120Y, and the like.

As described above, the liquid measuring device 110Y according to this embodiment, includes: a float 116Y that is moved in accordance with the liquid surface; the first magnetic field generator 117Y that is disposed in the float 116Y and positions its north (N) pole to face a first direction; the second magnetic field generator 118Y that is disposed in the float 116Y to be spaced apart from the first magnetic field generator 117Y and positions its south (S) pole to face the first direction; and the plurality of proportional output-type hole elements 113Y, 114Y, and 115Y that detect magnetic fields generated by the first magnetic field generator 117Y and the second magnetic field generator 118Y in positions facing the first direction. Accordingly, the liquid level can be continuously measured in accordance with a proportional output, and the amount of shortage of the liquid can be detected as a continuous value. Therefore, the liquid level of the liquid can be precisely measured.

In addition, the liquid measuring device 110Y includes the float supporting member 111Y that guides movement of the float 116Y and the regulating member 112Y that regulates the movement of the float 116Y. Accordingly, limit points can be detected, and thus overflow and the like can be prevented.

In addition, the liquid developer storing apparatus according to an embodiment of the invention includes the liquid developer storing unit 71Y that stores liquid developer containing toner particles in a carrier liquid and the liquid measuring device 110Y including: the float 116Y that is moved in accordance with a liquid surface of the liquid developer inside the liquid developer storing unit 71Y; the first magnetic field generator 117Y that is disposed in the float 116Y and positions its north (N) pole to face a first direction; the second magnetic field generator 118Y that is disposed in the float 116Y to be spaced apart from the first magnetic field generator 117Y and positions its south (S) pole to face the first direction; and the plurality of proportional output-type hole elements 113Y, 114Y, and 115Y that detect magnetic fields generated by the first magnetic field generator 117Y and the second magnetic field generator 118Y in positions facing the first direction. Accordingly, the liquid level of the liquid developer can be continuously measured in accordance with the proportional output, and the amount of shortage of the liquid developer can be detected as a continuous value. Therefore, the liquid level of the liquid developer can be measured precisely.

In addition, the liquid developer storing apparatus includes the density measuring unit 130Y including: the transparent propeller 122Y that can be moved within the liquid developer storing unit 71Y; the light emitting diode (LED) 131Y; the density-measuring light receiving element 132Y that receives light emitted by the light emitting diode (LED) 131Y; a gap 130aY in which the transparent propeller 122Y can be moved between the light emitting diode (LED) 131Y and the density-measuring light receiving element 132Y; and the density measuring unit 130Y that measures the density of the liquid developer based on the output of the density-measuring light receiving element 132Y for a case where the transparent propeller 122Y is located in the gap 130aY and a case where the transparent propeller 122Y is not located in the gap 130aY. Accordingly, the liquid developer can be precisely adjusted to have the liquid amount and density that are needed.

In addition, the liquid developer storing apparatus includes the float supporting member 111Y that guides movement of the float 116Y and the regulating member 112Y that is disposed in the density measuring unit 130Y and regulates the movement of the float 116Y. Accordingly, limit points can be detected, and thus overflow and the like can be prevented.

In addition, the image forming apparatus according to an embodiment of the invention includes: the developer container 31Y; the developing roller or developer carrier 20Y that carries liquid developer; the developer supplying roller or developer supplying member 32Y that supplies the liquid developer stored in the developer container 31Y to the developer carrier 20Y; the image carrier 10Y on which a latent image is developed by the developer carrier 20Y; the transfer body 40 on which the image on the image carrier 10Y is transferred; the liquid developer storing unit 71Y in which the liquid developer is stored; and the liquid measuring device 110Y that includes the float 116Y that is moved in accordance with a liquid surface of the liquid developer inside the liquid developer storing unit 71Y, the first magnetic field generator 117Y that is disposed in the float 116Y and positions its north (N) pole to face a first direction, the second magnetic field generator 118Y that is disposed in the float 116Y to be spaced apart from the first magnetic field generator 117Y and positions its south (S) pole to face the first direction, and the plurality of proportional output-type hole elements 113Y, 114Y, and 115Y that detect magnetic fields generated by the first magnetic field generator 117Y and the second magnetic field generator 118Y in positions facing the first direction. Accordingly, the amount of shortage of the liquid developer can be detected as a continuous value by continuously measuring the liquid level of the liquid developer in accordance with a proportional output. In addition, the liquid level of the liquid developer can be precisely detected. Therefore an image having an excellent image quality can be formed.

In addition, the image forming apparatus includes the position adjusting mechanism 150Y that adjusts the position of the liquid measuring device 110Y in the vertical direction, and accordingly, the degree of freedom for design can be increased.

In addition, the image forming apparatus includes the developer supplying path 81Y through which the liquid developer is supplied from the liquid developer storing unit 71Y of the liquid developer to the developer container 31Y, and the plurality of proportional output-type hole elements 113Y, 114Y, and 115Y is disposed in the developer supplying path 61Y. Accordingly, the precision of detection can be improved.

In addition, the image forming apparatus includes the density measuring device 120Y having: the transparent propeller 122Y that can be moved within the liquid developer storing unit 71Y; the light emitting diode (LED) 131Y; the density-measuring light receiving element 132Y that receives light emitted by the light emitting diode (LED) 131Y; the gap 130aY in which the transparent propeller 122Y can be moved between the light emitting diode (LED) 131Y and the density-measuring light receiving element 132Y; and the density measuring unit 130Y that measures the density of the liquid developer based on output of the density-measuring light receiving element 132Y for a case where the transparent propeller 122Y is located in the gap 130aY and a case where transparent propeller 122Y is not located in the gap 130aY and a wiring 138Y of the density measuring device 120Y which is disposed along the developer supplying path 81Y. Accordingly, the number of components can be decreased and the wiring 138Y can be maintained in a stable manner.

In addition, the image forming apparatus includes: the collecting path 72Y through which the liquid developer is collected into the liquid developer storing unit 71Y; the agitating propeller 123Y that agitates the liquid developer inside the liquid developer storing unit 71Y; and the agitating propeller shaft 121Y that supports the agitating propeller 123Y to be rotatable, and the agitating propeller 123Y is disposed to be overlapped with the collecting path 72Y, viewed from the direction of the agitating propeller shaft 121Y. Accordingly, the liquid developer that is newly collected or supplied can be agitated in a speedy manner.

In addition, in the image forming apparatus, the float 116Y has an opposing face that faces the plurality of proportional output-type hole elements 113Y, 114Y, and 115Y. Accordingly, the precision of the hole elements 113Y, 114Y, and 115Y can be improved by decreasing the flow of the liquid developer.

In addition, in the image forming apparatus, the float 116Y has the end part 116aY having a rounded acute-angled shape on the opposite side of the opposing face, and accordingly, the liquid developer can be easily flown.

In addition, the image forming apparatus includes: the liquid-level determining unit 210Y that determines the liquid amount measured by the liquid measuring device 110Y; the liquid-level control unit 201Y that controls the liquid amount based on the result of determination of the liquid-level determining unit 210Y; the density determining unit 220Y that determines the density measured by the density measuring device 120Y; the density control unit 202Y that controls the density of the liquid developer of the liquid developer storing unit 71Y in accordance with the result of determination of the density determining unit 220Y; and the selection unit 200Y that selects one between the liquid-level control unit 201Y and the density control unit 202Y. Accordingly, the image forming apparatus can be controlled in accordance with the liquid amount and density of the liquid developer, and thereby an image having excellent image quality can be formed in accordance with the state of the liquid developer.

In addition, the image forming apparatus includes the sending amount calculating unit 200Y that prohibits input of the liquid by using the liquid-level control unit 201Y in a case where the liquid amount measured by the liquid measuring device 110Y is larger than a predetermined amount, and accordingly, overflow and the like can be prevented.

In addition, the image forming apparatus includes the sending amount calculation unit 200Y that stops printing by using the density determining unit 220Y in a case where the density measured by the density measuring device 120Y is higher than the first predetermined density or lower than the second predetermined density that is set lower than the first predetermined density. Accordingly, an image having deteriorated image quality is not formed.

The entire disclosure of Japanese Patent Application Nos: 2007-224228, filed Aug. 30, 2007 and 2008-167191, filed Jun. 26, 2008 are expressly incorporated by reference herein.

What is claimed is:

1. A liquid measuring device comprising:
  a floating member that is moved in accordance with a level of liquid;
  a first magnetic field generator that is disposed in the floating member and positions its north (N) pole to face a first direction;
  a second magnetic field generator that is disposed in the floating member to be spaced apart from the first magnetic field generator and positions its south (S) pole to face the first direction; and
  a proportional output-type hole element that detects magnetic fields generated by the first magnetic field generator and the second magnetic field generator in a position facing the first direction.

2. The liquid measuring device according to claim 1, further comprising:
  a guiding unit that guides movement of the floating member; and
  a regulating member that regulates the movement of the floating member.

3. A liquid developer storing apparatus comprising:
  a storage unit that stores liquid developer containing toner particles in a carrier liquid; and
  a liquid measuring device including:
  a floating member that is moved in accordance with a level of liquid of the liquid developer inside the storage unit;
  a first magnetic field generator that is disposed in the floating member and positions its north (N) pole to face a first direction;
  a second magnetic field generator that is disposed in the floating member to be spaced apart from the first magnetic field generator and positions its south (S) pole to face the first direction; and
  a proportional output-type hole element that detects magnetic fields generated by the first magnetic field generator and the second magnetic field generator in a position facing the first direction.

4. The liquid developer storing apparatus according to claim 3, further comprising a density measuring device including:
  a moving member that can be moved within the storage unit;
  a light emitting member;
  a light receiving member that receives light emitted by the light emitting member;
  a gap part in which the moving member can be moved between the light emitting member and the light receiving member; and
  a density measuring unit that measures the density of the liquid developer based on the output of the light receiving member for a case where the moving member is located in the gap part and a case where the moving member is not located in the gap part.

5. The liquid developer storing apparatus according to claim 4, further comprising:
  a guiding unit that guides movement of the floating member; and
  a regulating member that is disposed in the density measuring unit and regulates the movement of the floating member.

6. An image forming apparatus comprising:
  a developer container;
  a developer carrier that carries liquid developer;
  a developer supplying member that supplies liquid developer stored in the developer container to the developer carrier;
  an image carrier on which a latent image is developed by the developer carrier;
  a transfer body on which the latent image on the image carrier is transferred;
  a storage unit in which the liquid developer is stored; and
  a liquid measuring device including;
  a floating member that is moved in accordance with a level of the liquid developer inside the storage unit;
  a first magnetic field generator that is disposed in the floating member and positions its north (N) pole to face a first direction;
  a second magnetic field generator that is disposed in the floating member to be spaced apart from the first magnetic field generator and positions its south (S) pole to face the first direction; and
  a proportional output-type hole element that detects magnetic fields generated by the first magnetic field generator and the second magnetic field generator in a position facing the first direction.

7. The image forming apparatus according to claim 6, further comprising a position adjusting mechanism that adjusts a position of the liquid measuring device in a vertical direction.

8. The image forming apparatus according to claim 6, further comprising a supply path through which the liquid developer is supplied from the storage unit to the developer container, wherein the proportional output-type hole element of the liquid measuring device is disposed in the supply path.

9. The image forming apparatus according to claim 8, further comprising:
a density measuring device including:
a moving member that can be moved within the storage unit;
a light emitting member;
a light receiving member that receives light emitted by the light emitting member;
a gap part in which the moving member can be moved between the light emitting member and the light receiving member; and
a density measuring unit that measures the density of the liquid developer based on output of the light receiving member for a case where the moving member is located in the gap part and a case where the moving part is not located in the gap part; and
a wiring of the density measuring device which is disposed along the supply path.

10. The image forming apparatus according to claim 9, further comprising:
a liquid-level determining unit that determines the liquid developer amount measured by the liquid measuring device;
a liquid-level control unit that controls the liquid amount based on the result of determination of the liquid-level determining unit;
a density determining unit that determines the density measured by the density measuring device;
a density control unit that controls the density of the liquid developer of the storage unit in accordance with the result of determination of the density determining unit; and
a selection unit that selects one between the liquid-level control unit and the density control unit.

11. The image forming apparatus according to claim 10, further comprising a sending amount calculating unit that prohibits input of the liquid developer by using a liquid-level control unit in a case where the liquid developer amount measured by the liquid developer measuring device is larger than a predetermined amount.

12. The image forming apparatus according to claim 10, further comprising a sending amount calculation unit that stops printing by using the density determining unit in a case where the density measured by the density measuring device is higher than a first predetermined density or lower than a second predetermined density that is set lower than the first predetermined density.

13. The image forming apparatus according to claim 6, further comprising:
a collection path through which the liquid developer is collected into the storage unit;
an agitating propeller that agitates the liquid developer inside the storage unit; and
an agitating propeller shaft that supports the agitating propeller to be rotatable,
wherein the agitating propeller is disposed to be overlapped with the collection path, viewed from the direction of the agitating propeller shaft.

14. The image forming apparatus according to claim 6, wherein the floating member has an opposing face that faces the proportional output-type hole element.

15. The image forming apparatus according to claim 14, wherein the floating member has an end part having a rounded acute-angled shape on the opposite side of the opposing face.

16. The image forming apparatus according to claim 6, the number of the proportional output-type hole element is two or more than two.

* * * * *